(12) United States Patent
Cook et al.

(10) Patent No.: US 8,263,647 B2
(45) Date of Patent: Sep. 11, 2012

(54) TREATMENT OF SLEEP DISTURBANCES

(75) Inventors: Graham D. Cook, Midlothian, VA (US);
Todd S. Koch, Powhatan, VA (US);
David H. Giamalva, Gleen Allen, VA
(US); Justin Bianco, Vineland, VA (US);
James J. Fort, Midlothian, VA (US);
Geraldine Doyle, Chatham, NJ (US);
Steven Cooper, Denville, NJ (US)

(73) Assignee: Wyeth LLC, Madison, NJ (US)

( * ) Notice: Subject to any disclaimer, the term of this patent is extended or adjusted under 35 U.S.C. 154(b) by 133 days.

(21) Appl. No.: 12/082,342

(22) Filed: Apr. 10, 2008

(65) Prior Publication Data

US 2009/0169584 A1 Jul. 2, 2009

Related U.S. Application Data

(63) Continuation of application No. 10/046,727, filed on Jan. 17, 2002, now abandoned.

(51) Int. Cl.
*A61K 31/192* (2006.01)
*A61K 9/00* (2006.01)
*A61K 31/36* (2006.01)
*A61K 31/19* (2006.01)

(52) U.S. Cl. ......... 514/464; 514/557; 514/570; 424/400

(58) Field of Classification Search .................. 514/464, 514/557
See application file for complete search history.

(56) References Cited

U.S. PATENT DOCUMENTS

| | | |
|---|---|---|
| 4,401,665 A | 8/1983 | Sheinaus |
| 4,420,483 A | 12/1983 | Sunshine et al. |
| 4,464,376 A | 8/1984 | Sunshine et al. |
| 4,522,826 A | 6/1985 | Sunshine et al. |
| 4,585,783 A | 4/1986 | Sunshine et al. |
| 4,683,243 A | 7/1987 | Sunshine et al. |
| 4,738,966 A | 4/1988 | Sunshine et al. |
| 4,755,532 A | 7/1988 | Sunshine et al. |
| 4,906,625 A | 3/1990 | Sunshine et al. |
| 4,985,459 A | 1/1991 | Sunshine et al. |
| 5,431,916 A | 7/1995 | White |
| 5,512,300 A | 4/1996 | Weng et al. |
| 6,063,405 A | 5/2000 | Drizen et al. |
| 6,165,500 A | 12/2000 | Cevc |
| 6,251,426 B1 | 6/2001 | Gullapalli |
| 6,287,600 B1 | 9/2001 | Ouali et al. |

FOREIGN PATENT DOCUMENTS

| | | |
|---|---|---|
| EP | 0 475 160 A1 | 3/1992 |
| WO | WO 97/11681 | 4/1997 |
| WO | WO 97/29735 | 8/1997 |

OTHER PUBLICATIONS

Drug Facts and Comparisons, 1997, Edition, p. 1143.*
Gengo, F. "The Effects of Ibuprofen on Polysomnographic and Subjective Measures of Sleep in Healthy Adults", J. Clin. Pharmacol., 36:859 (1996).
Gengo, F. "The Pharmacodynamics of Diphenhydramine-induced Drowsiness and Changes in Mental Performance", Clin. Pharmacol. Ther., vol. 45:15-21 (1989).
Lavie, et al., "Effects of Midazolam on Sleep Disturbances Associated with Westward and Eastward Flights: Evidence for Directional Effects", Psychopharmacology, vol. 101-250-254 (1990).
Murphy, et al. "Nonsteroidal Anti-Inflammatory Drugs Affect Normal Sleep Patterns in Humans", Physiology & Behavior, vol. 55:1063-1066 (1994).
"Soft Capsules", Encyclopedia of Pharmaceutical Technology, 269-276, (Swarbrick ed. (1988)).
"Soft Gelatin Capsules", Pharmaceutical Dosage Forms & Drug Delivery Systems, 176-179 (Ansel ed. $6^{th}$ ed. (1995)).
Stanley, J.P., "Soft Gelatin Capsules", The Theory and Practice of Industrial Pharmacy, 398-412, (Lachman ed. $3^{rd}$ ed. (1986)).
Sunshine, A. "Hypnotic Activity of Diphenhydramine, Methapyriline, and Placebo", J. Clin. Pharmacology, Aug.-Sep.: 425-431 (1978).
Drug Facts and Comparisons, 1997, Edition,pp. 1135-1142 and 2387-1389.

* cited by examiner

*Primary Examiner* — Jennifer M Kim
(74) *Attorney, Agent, or Firm* — Jeffrey Gold, Esq.; Stephanie Monaco, Esq.; Joseph Mazzarese, Esq.

(57) ABSTRACT

The present invention provides a new composition for treating pain-associated sleep disturbances, especially shortened sleep duration, comprising ibuprofen and diphenhydramine. The composition is further prepared as a bilayer tablet or caplet, or alternatively as a soft gelatin capsule composition, to prevent interaction between the active ingredients.

18 Claims, 29 Drawing Sheets

TREATMENT OF SLEEP DISTURBANCES

CROSS-REFERENCE TO RELATED APPLICATIONS

This application is a continuation of application Ser. No. 10/046,727 filed on Jan. 17, 2002 now abandoned.

FIELD OF THE INVENTION

This invention relates to the treatment of sleep disturbances. The invention further relates to the treatment of sleep disturbances associated with pain, including, for example, sleep disturbances resulting in a shortened sleep duration.

BACKGROUND OF THE INVENTION

Many people suffer from sleep disturbances, which can result in significant consequences to the health of an individual. Sleep-deprived individuals can have significantly impaired daytime cognition and motor performance. One recognized result of such sleep deprivation is an increase in automobile accidents. The National Highway Traffic Safety Administration estimates that 100,000 car crashes a year are linked to sleepy driving. Nanci Hellmich, "*Balancing Act*," TULSA WORLD, Jun. 2, 2000.

Sleep disturbances associated with pain are especially problematic. Individuals suffering from pain-associated sleep disturbances often have great difficulty staying asleep (sleep duration), and hence getting enough rest during the night. Sleep duration is very important to the physical and mental health of the individuals involved. Because so many individuals suffer from pain-associated sleep disturbances, especially shortened sleep duration, there is a need for a medication to treat these conditions. By pain-associated sleep disorders we mean difficulties falling asleep (i.e., longer time until patient falls asleep) and difficulties saying asleep (i.e., waking too early, before a full night sleep), where either or both of these difficulties are present with or exacerbated by bodily pain, including, but not limited to headache, muscle aches and pain, sore throat, sinus pain, menstrual cramps, back pain, toothache, arthritis.

Ibuprofen, a propionic acid derivative nonsteroidal antiinflammatory drug (NSAID), has been used in the treatment of pain, injury, and illness for its analgesic, antiinflammatory, and antipyretic effects. It is taken for arthritis, sports injuries, soft tissue trauma, dysmenorrhea, migraine headaches, tension headaches, and dental pain, for example. Ibuprofen is one of the most extensively studied and widely used drugs. It has been estimated that ibuprofen has been used to treat over 100 million patients in at least 100 countries throughout the world. Ibuprofen a very widely used drug in the world. The NSAID ibuprofen has the following chemical structure:

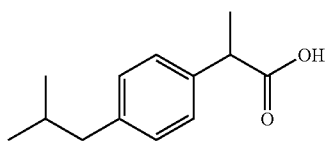

About 80% of an oral dose of ibuprofen in humans is absorbed from the GI tract. Following oral administration, peak serum concentrations are reached within 1 or 2 hours, for suspensions and tablets, respectively. The plasma half-life of ibuprofen has reported to be about 2 hours. The recommended nonprescription dose of ibuprofen for adults is 200 mg every 4 to 6 hours while symptoms persist. If the symptoms do not respond to 1 tablet (200 mg), then 2 tablets can be used. However, no more than 6 tablets should be taken in 24 hours unless directed by a physician. Higher levels of ibuprofen can be used for a prescription product, yielding a dose of 600 or 800 mg every 4 to 6 hours.

Ibuprofen has not previously been known to improve sleep. In fact, quite the opposite, ibuprofen has been shown in some studies of patients not suffering from pain to hinder sleep. Murphy et al., "*Nonsteroidal Anti-Inflammatory Drugs Affect Normal Sleep Patterns in Humans*," PHYSIOLOGY & BEHAVIOR 55:1063-1066 (1994). Ibuprofen has been shown to increase the number of awakenings and percentage of time spent in stage wake, and decrease sleep efficiency. Ibuprofen has also been shown to delay the onset of deeper stages of sleep. Ibuprofen was thought to have this effect by decreasing prostaglandin synthesis, reducing melatonin synthesis, and changing body temperature. Id. Other studies indicate that ibuprofen has no impact on sleep. Gengo, "*The Effects of Ibuprofen on Polysomnographic and Subjective Measures of Sleep in Healthy Adults*," J. CLIN. PHARMACOL. 36:859 (1996).

Diphenhydramine hydrochloride (2-(diphenylmethoxy)-N,N-dimethylethylamine) is an ethanolamine $H_1$ blocking agent. It antagonizes histamine effects on receptor sites. Diphenhydramine has sedative, antiemetic, anticholinergic, anti-motion sickness, antitussive, CNS excitation and CNS depression, and local anesthetic properties as well. Diphenhydramine hydrochloride and diphenhydramine citrate, two common forms, have the following chemical structures:

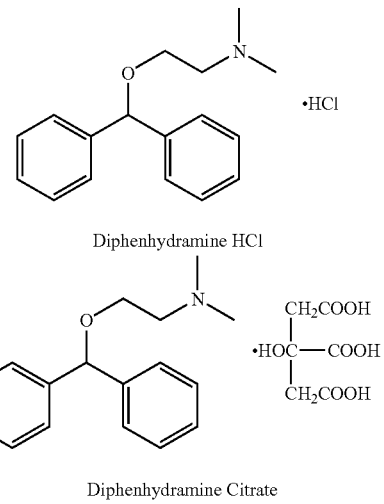

Diphenhydramine HCl

Diphenhydramine Citrate

The drugs in this group are potent and effective $H_1$ blockers that possess significant antimuscarinic activity and have a pronounced tendency to induce sedation. With conventional doses, about half of those who are treated with drugs in this class experience somnolence. Diphenhydramine has been primarily used for its antihistamine properties, but it has also been used for its somnolent effect and for treatment of motion sickness. There have also been some reports of weak analgesic effects.

Diphenhydramine is well absorbed following oral administration. Following oral administration of a single dose of diphenhydramine, the drug appears in plasma within 15 minutes, and peak plasma concentrations are attained within 1.5 to 4 hours. The usual dose of diphenhydramine as a nighttime sleep aid is 50 mg of diphenhydramine hydrochloride, or an equivalent 76 mg diphenhydramine citrate.

Although diphenhydramine is well-known as a nighttime sleep aid, there exists a need for improved medications for the treatment of sleep disturbances, and in particular, pain-associated sleep disturbances.

SUMMARY OF THE INVENTION

It has surprisingly been discovered that a special formulation of ibuprofen and diphenhydramine results in an effective treatment for sleep disturbances, and in particular, pain-associated sleep disturbances, without having negative interactions between the two active ingredients during formulation or while the composition is on the shelf. These results were particularly surprising in view of the prior studies' suggestion that ibuprofen had no effect, or an adverse effect, on sleep.

Applicants have recently discovered that the combination of ibuprofen and diphenhydramine not only is effective in the treatment of pain, but also is effective in the treatment of sleep disturbances, especially in addressing the problem of shortened sleep duration. Applicants have also discovered that ibuprofen and diphenhydramine have the potential for negative interaction in a pharmaceutical composition.

The present invention provides a composition and a method of making the composition for the treatment of pain-associated sleep disturbances comprising ibuprofen and diphenhydramine in amounts effective to treat a pain associated sleep disturbance or wherein the composition is sufficiently chemically and physically stable. Another embodiment of the invention provides a composition for the treatment of pain-associated sleep disturbances comprising ibuprofen and diphenhydramine, wherein the composition is formulated to avoid the risk of drug interaction. The invention also provides a method of treating patients with pain-associated sleep disturbances.

One embodiment of the present invention provides compositions comprising ibuprofen and diphenhydramine in amounts effective to treat a pain-associated sleep disturbance. Another embodiment of the present invention provides compositions comprising ibuprofen and diphenhydramine in amounts effective to treat a pain-associated sleep disturbance, wherein the composition is a bilayer tablet, bilayer caplet, or soft gelatin capsule. Another embodiment of the present invention provides methods for treating a patient suffering from a sleep disturbance comprising administering the composition of the invention and allowing the composition to treat the sleep disturbance. A further embodiment of this invention provides a composition for the treatment of pain-associated sleep disturbances comprising ibuprofen and diphenhydramine, wherein the pain-associated sleep disturbances include difficulties falling asleep and difficulties staying asleep.

DETAILED DESCRIPTION

Figure 1:
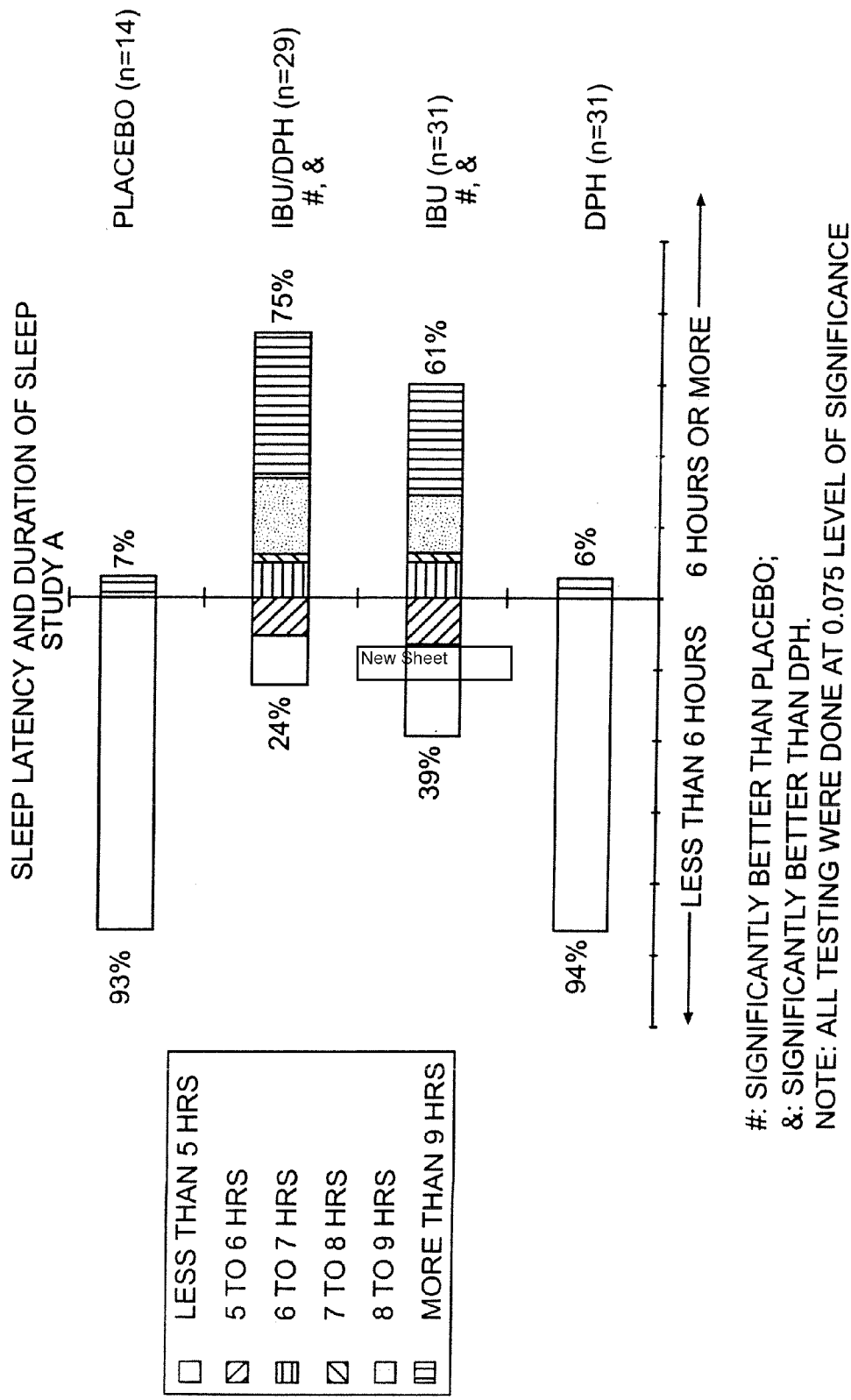
FIG. 1: This figure shows the duration of sleep results for Study A.
Figure 2:
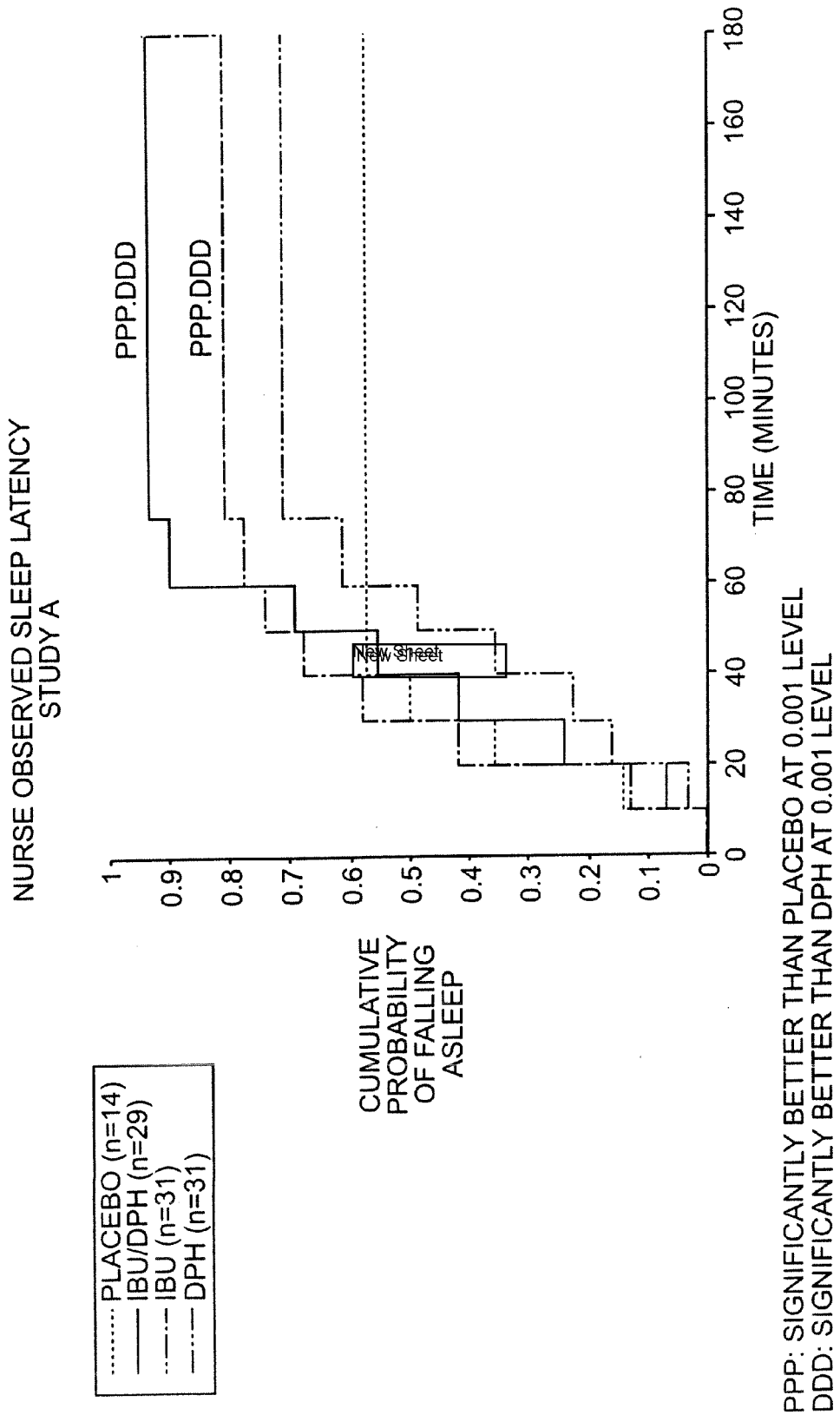
FIG. 2: This figure shows the nurse observed sleep latency results from Study A. Both the ibuprofen and combination groups were significantly better than the diphenhydramine and placebo groups.
Figure 3:
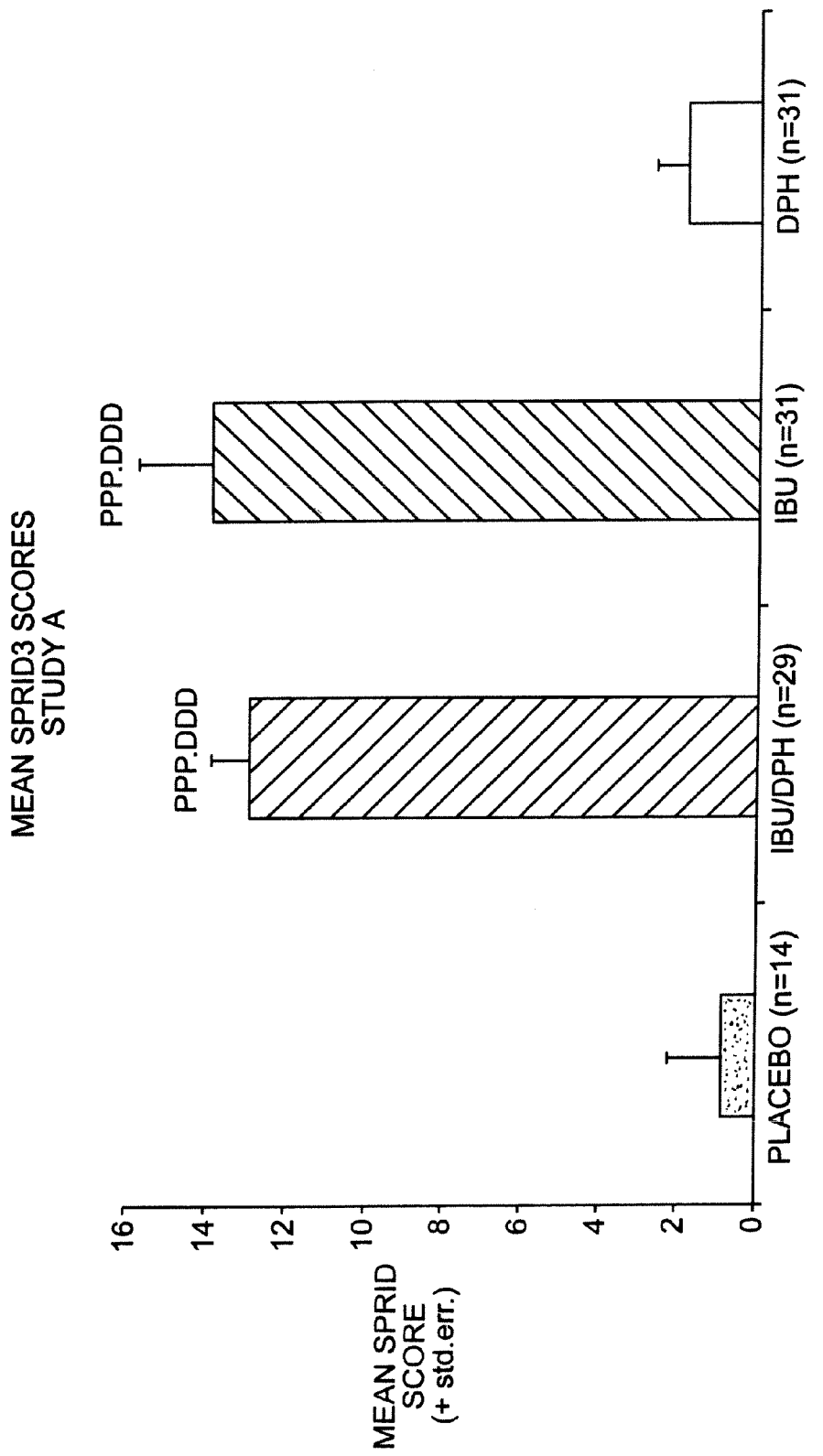
FIG. 3: This figure shows the mean SPRID3 scores for Study A.
Figure 4:
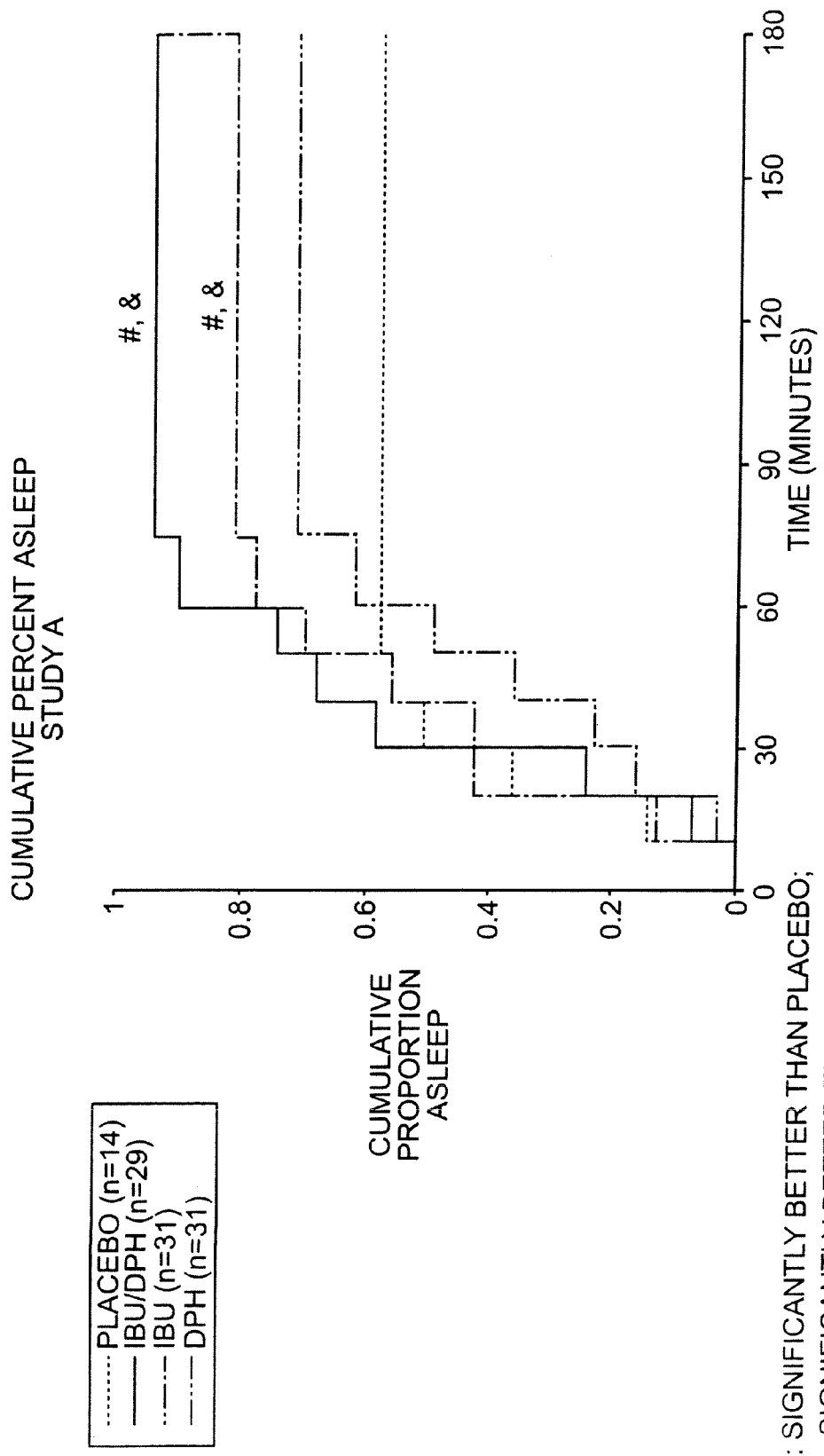
FIG. 4: This figure shows the cumulative percent of patients asleep for Study A.
Figure 5:
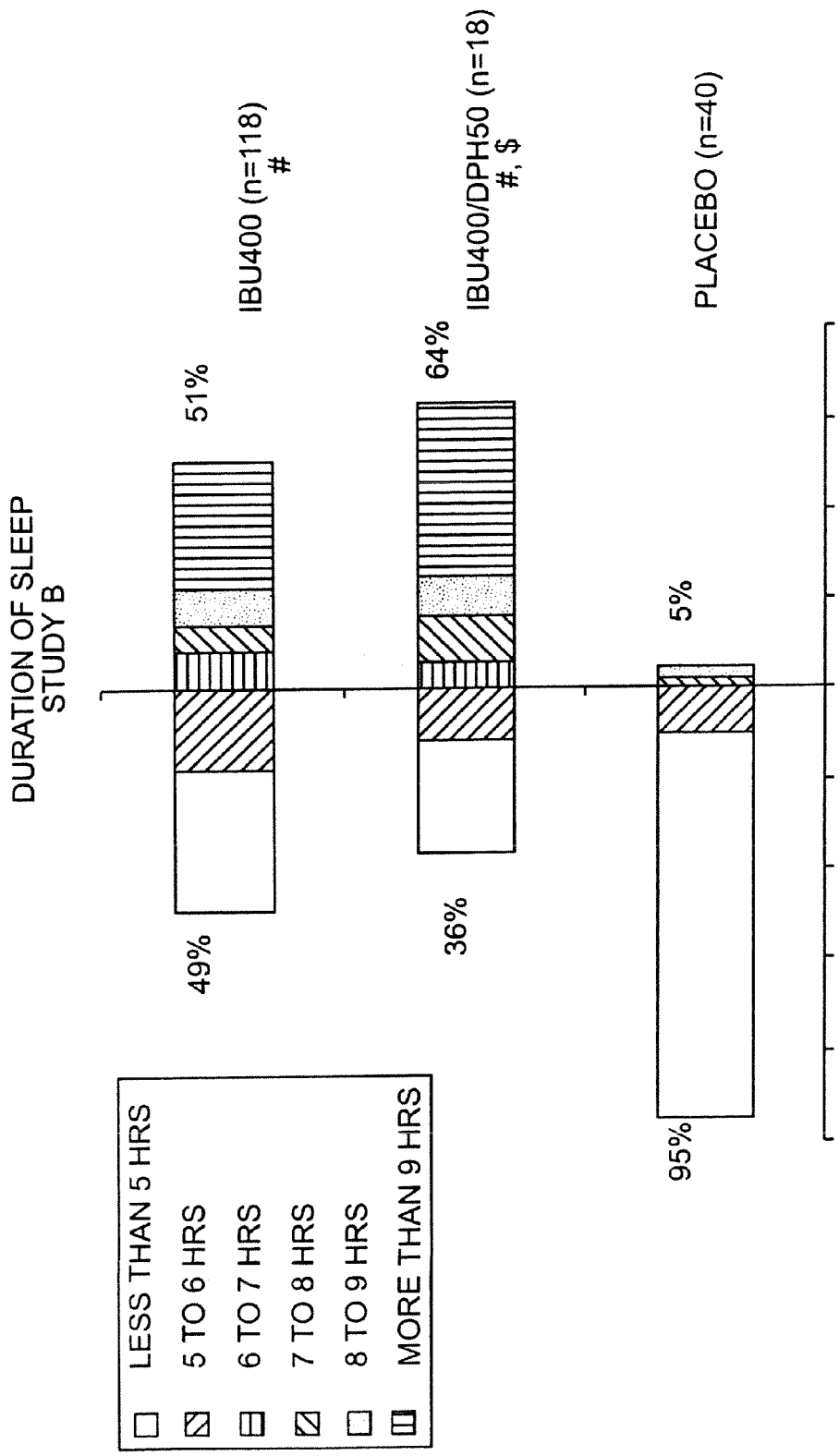
FIG. 5: This figure shows the duration of sleep data for Study B.
Figure 6:
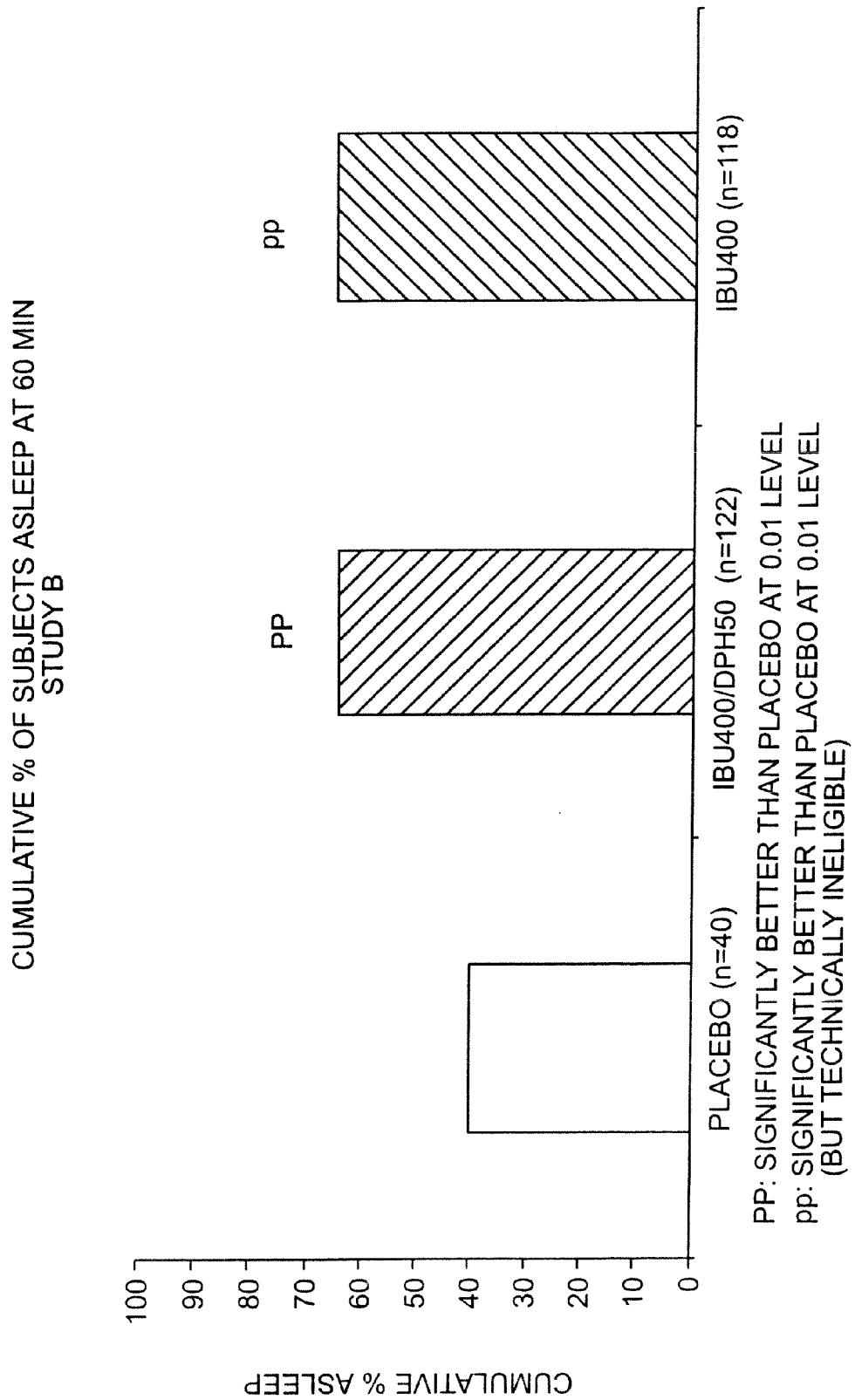
FIG. 6: This figure shows the cumulative percent of patients asleep for Study B.
Figure 7:
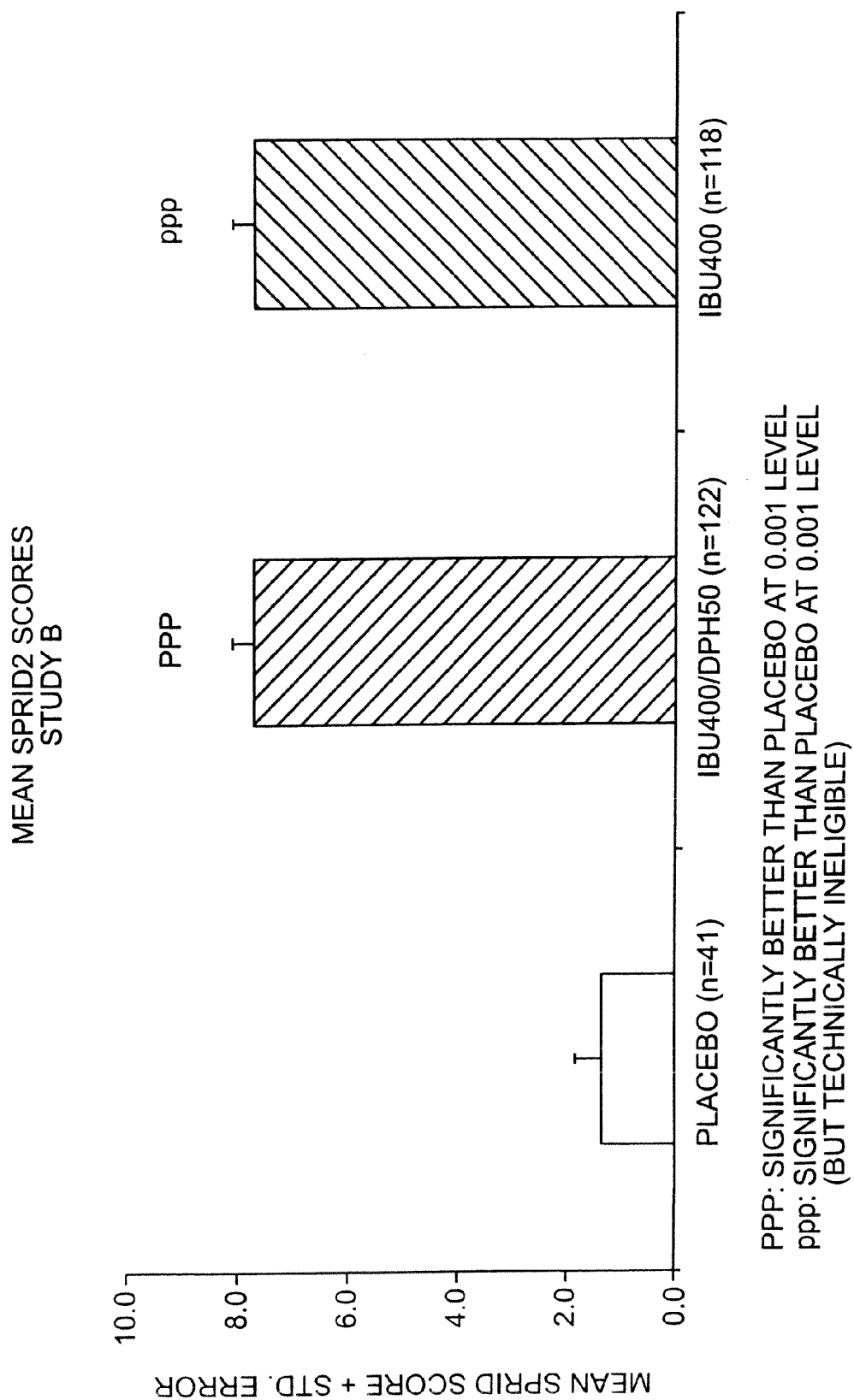
FIG. 7: This figure shows the mean SPRID2 scores for Study B.
Figure 8:
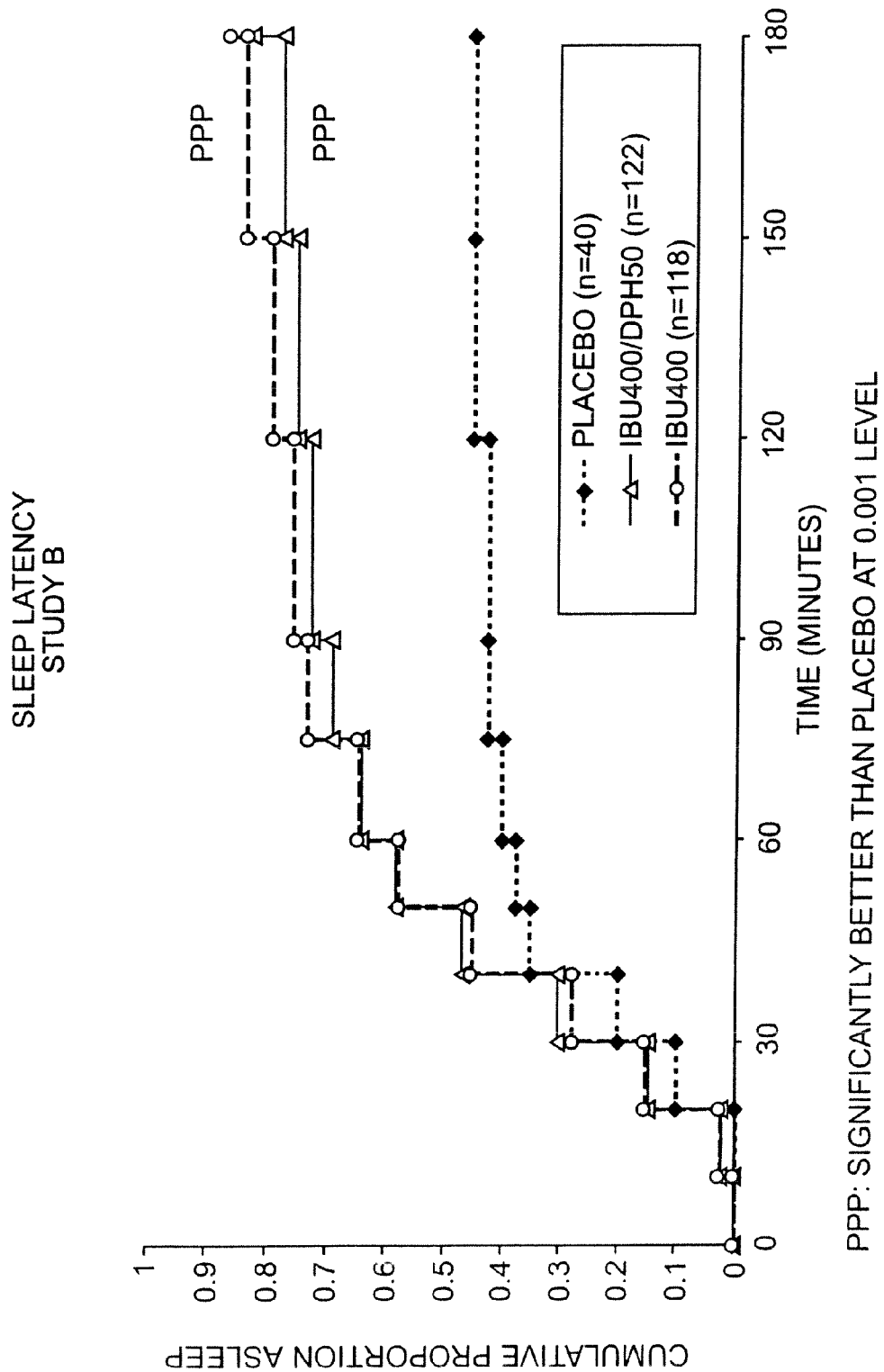
FIG. 8: This figure shows the nurse observed sleep latency results for Study B.
Figure 9:
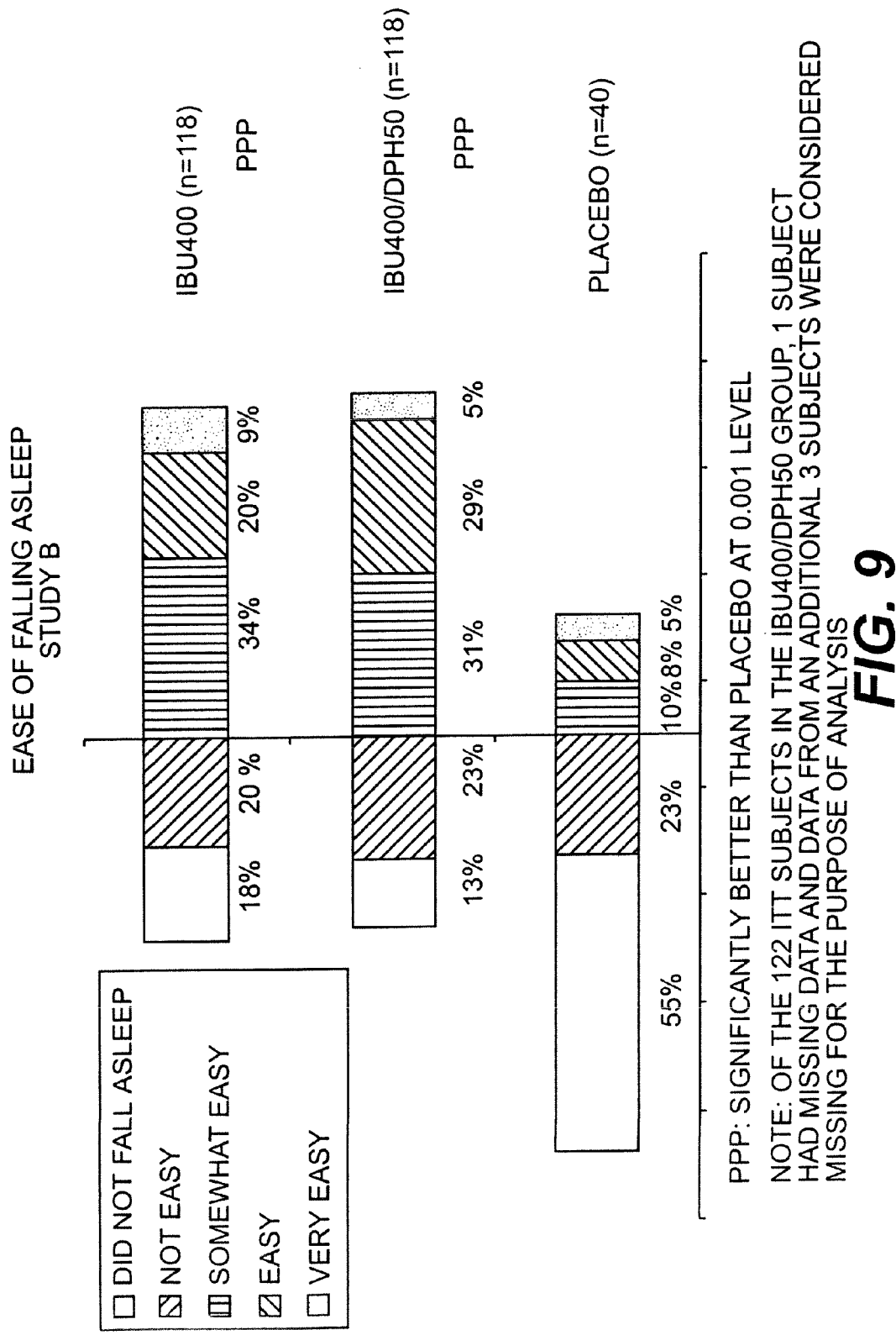
FIG. 9: This figure shows the ease of falling asleep data for Study B.
Figure 10:
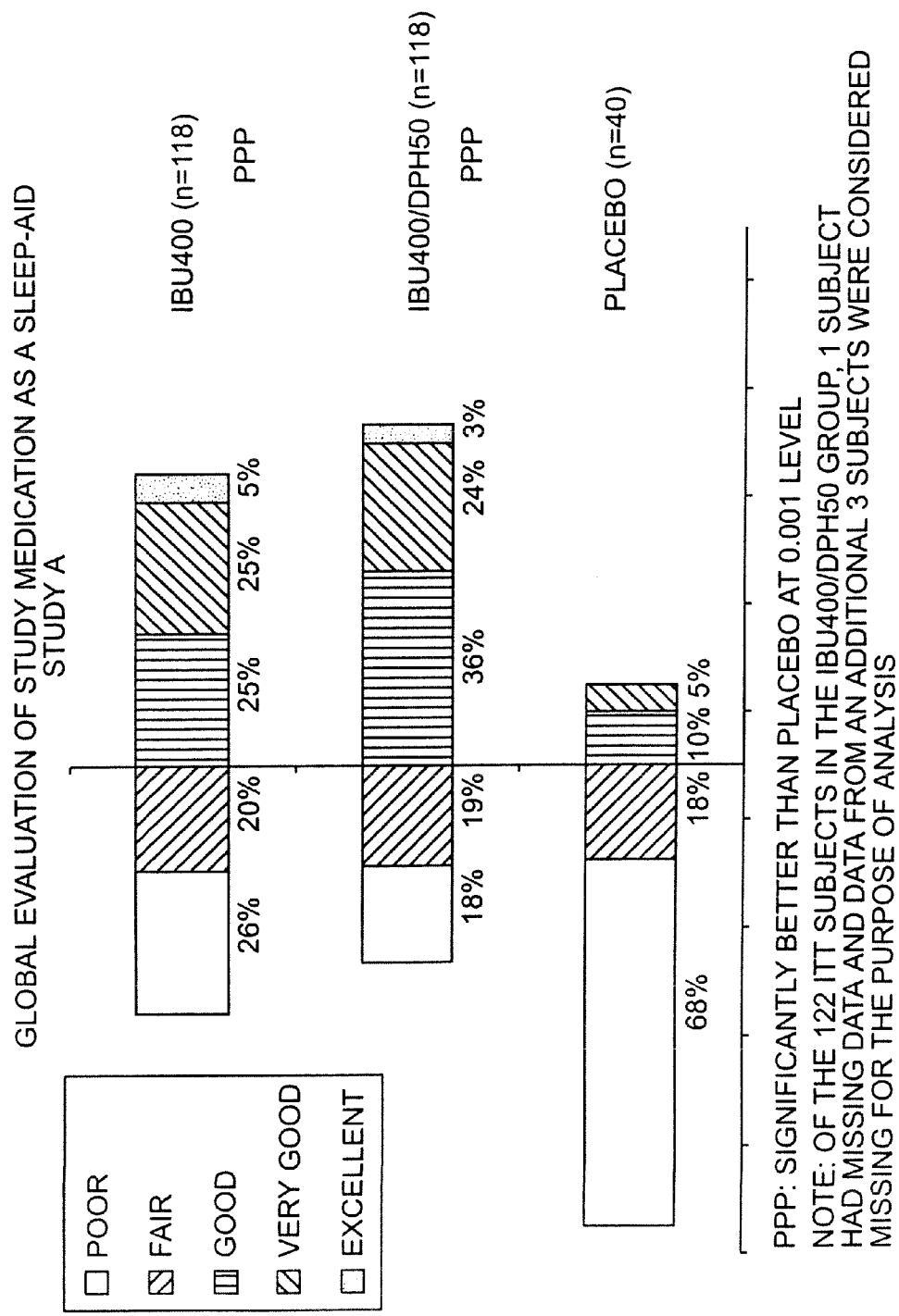
FIG. 10: This figure shows the data from the global evaluation of the study medication as a sleep aid for Study B.
Figure 11:
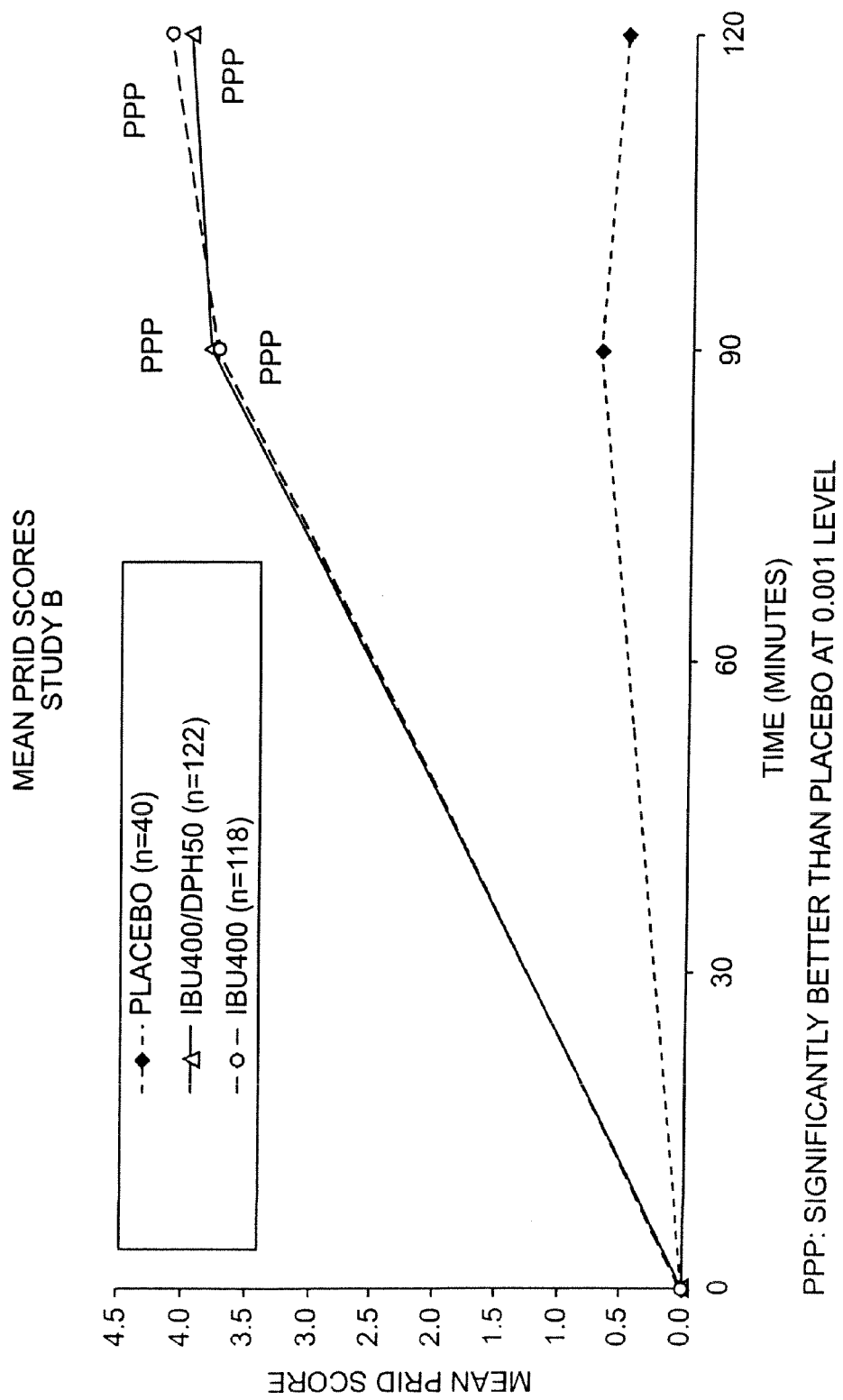
FIG. 11: This figure shows the PRID scores for Study B.
Figure 12:
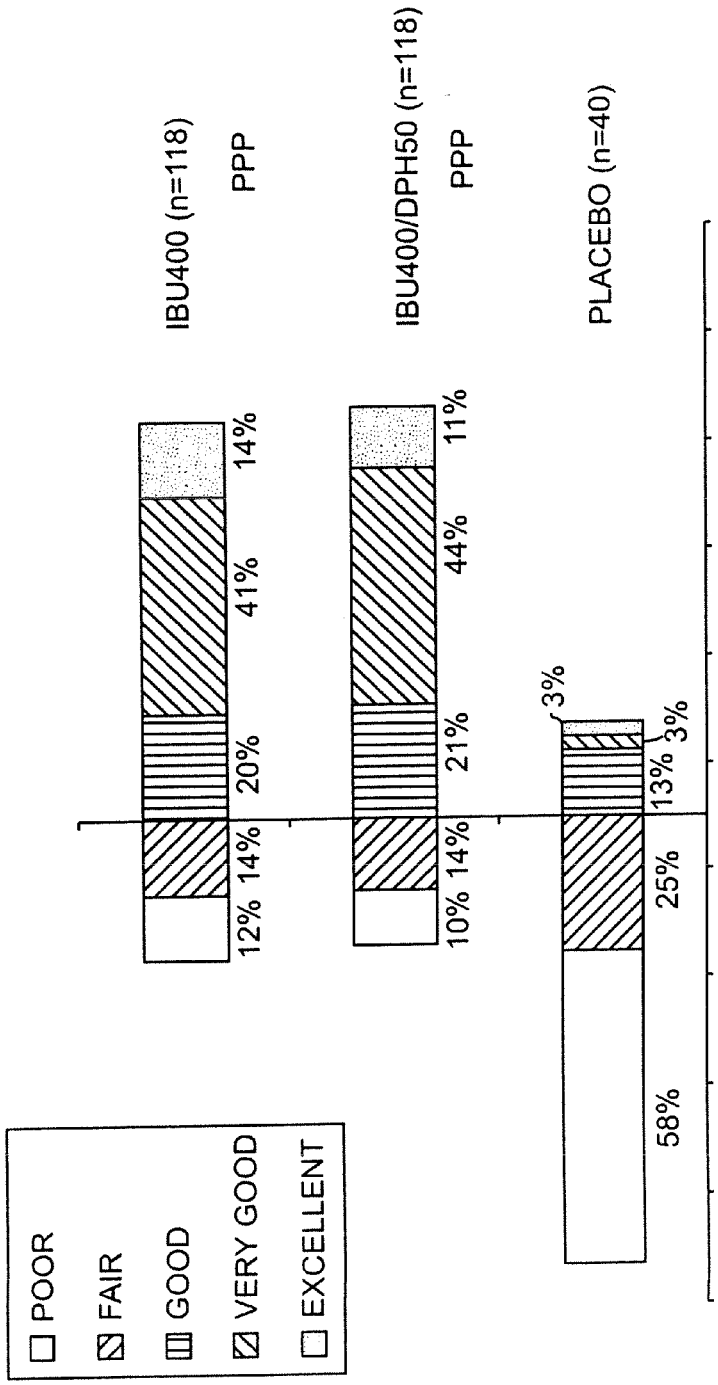
FIG. 12: This figure shows the global evaluation of the study medication as a pain reliever for Study B.
Figure 13:
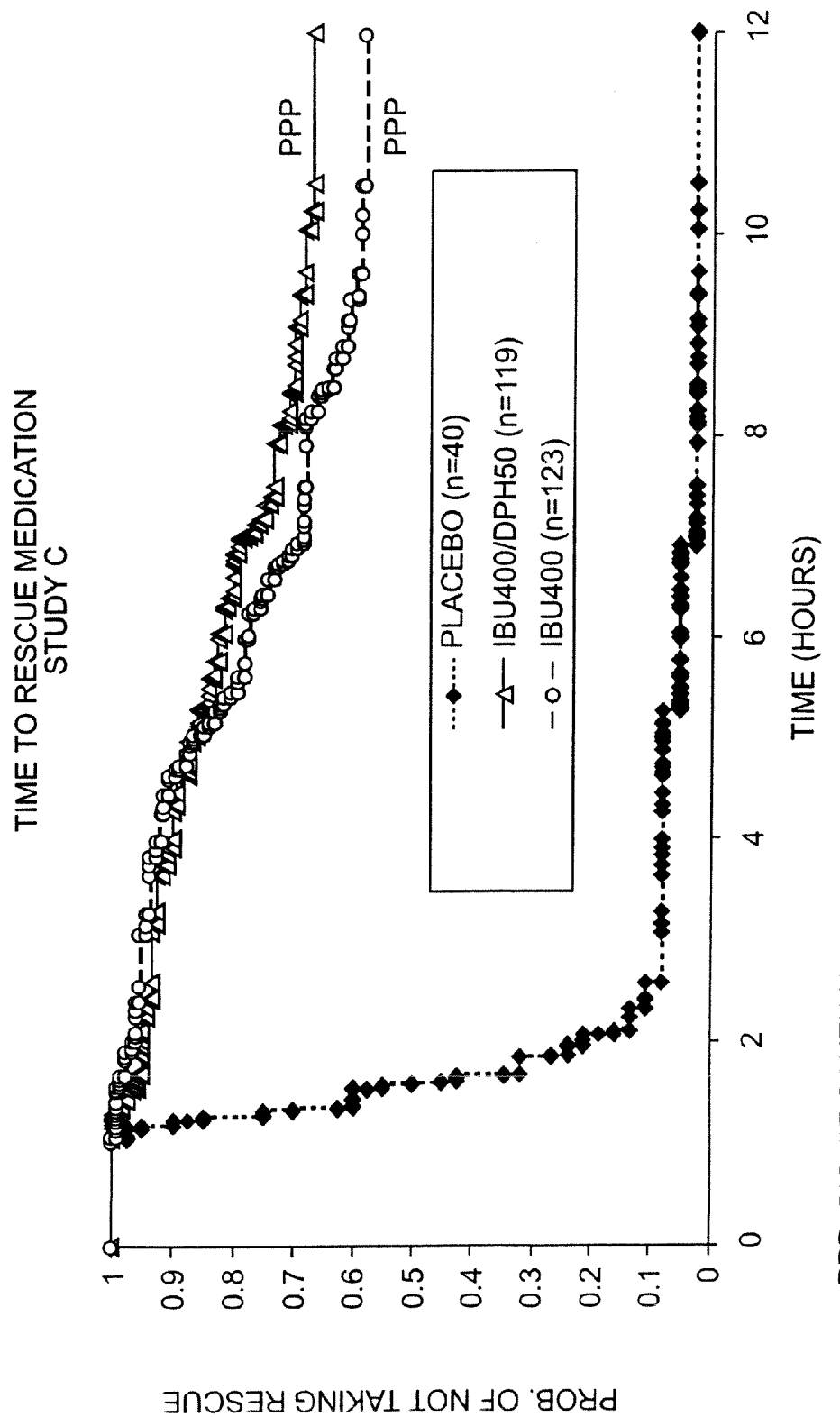
FIG. 13: This figure shows the time to rescue medication for any reason for Study C.
Figure 14:
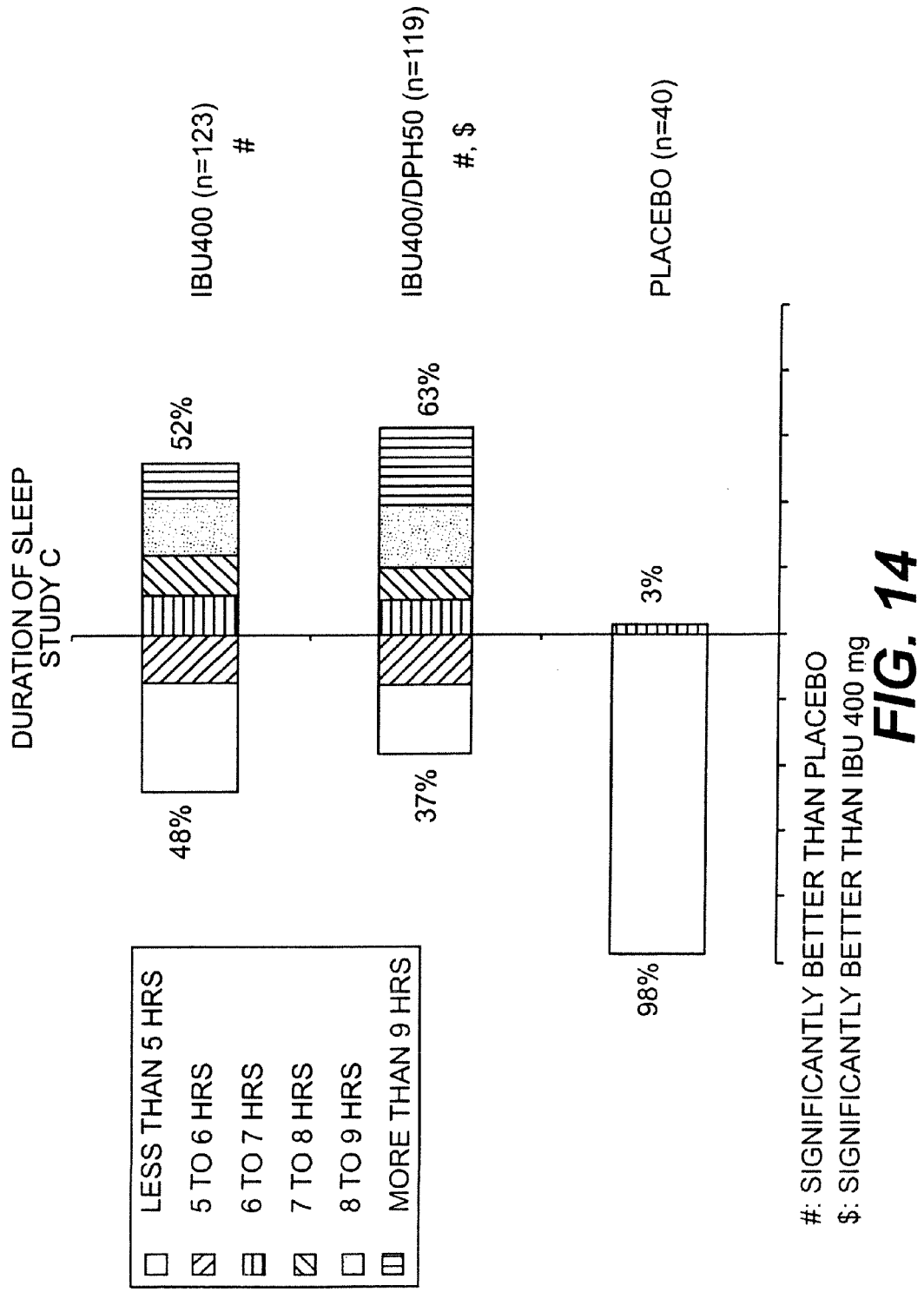
FIG. 14: This figure shows the duration of sleep data for Study C.
Figure 15:
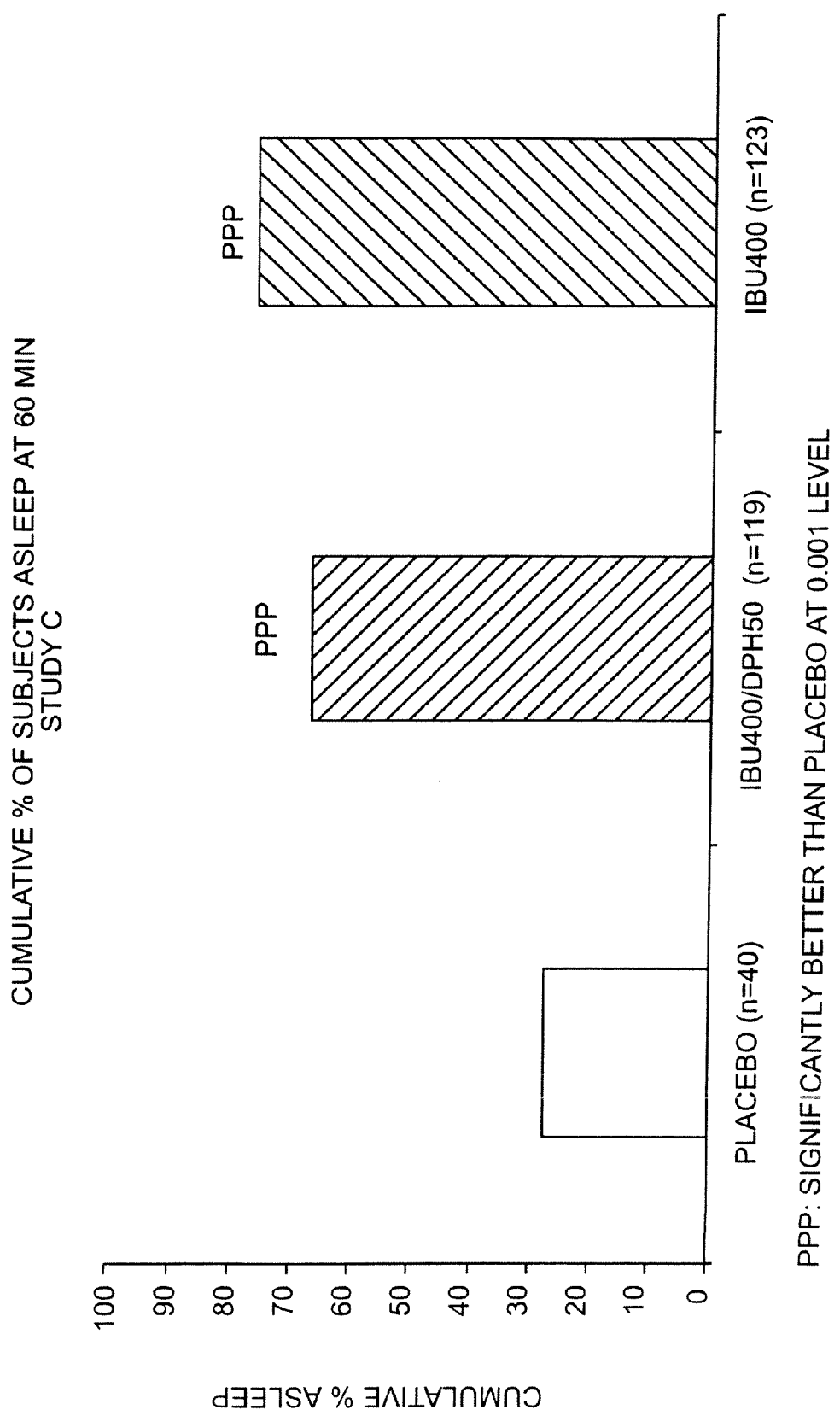
FIG. 15: This figure shows the cumulative percent asleep by 60 minutes for Study C.
Figure 16:
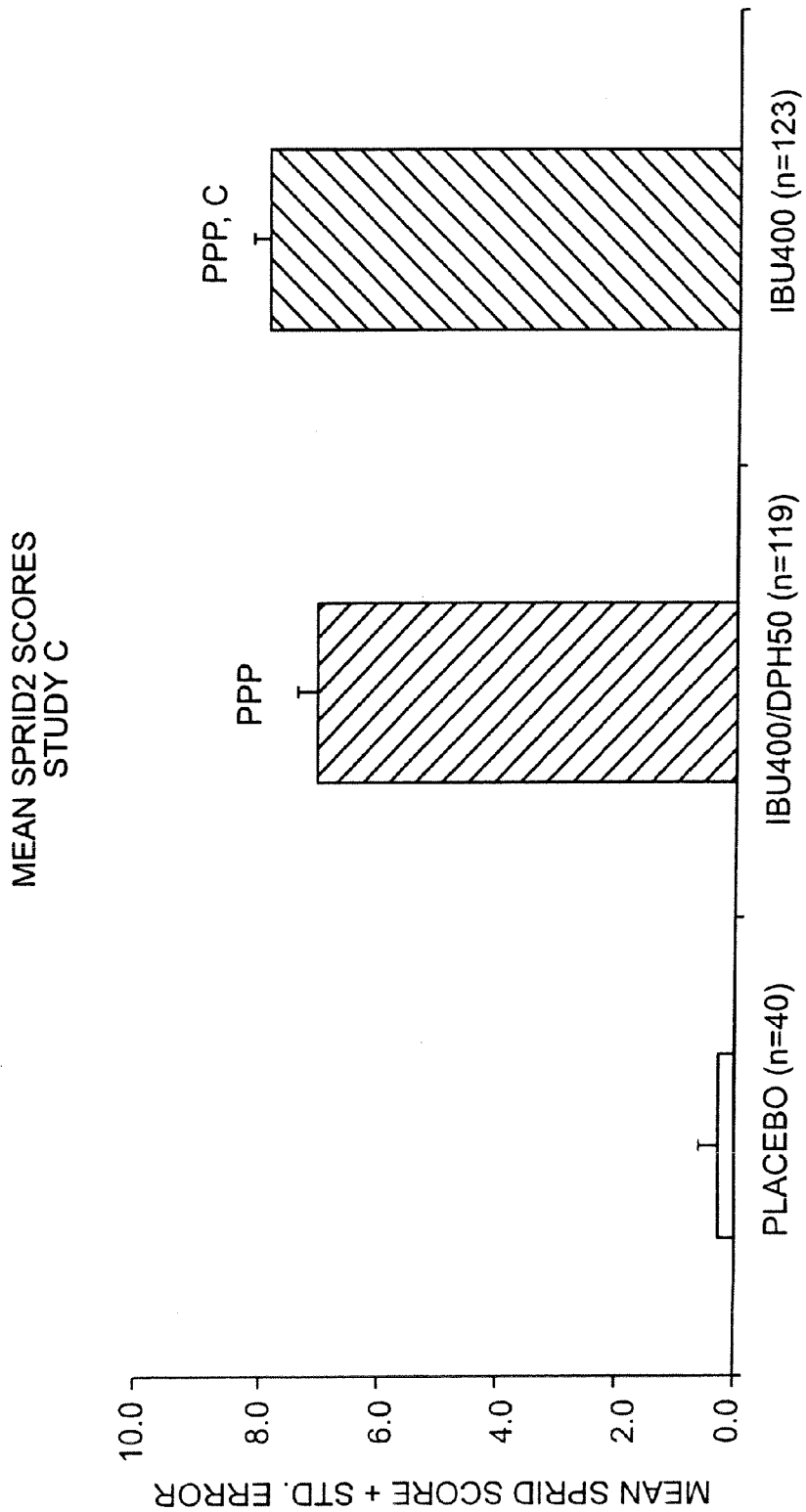
FIG. 16: This figure shows the SPRID2 scores for Study C.
Figure 17:
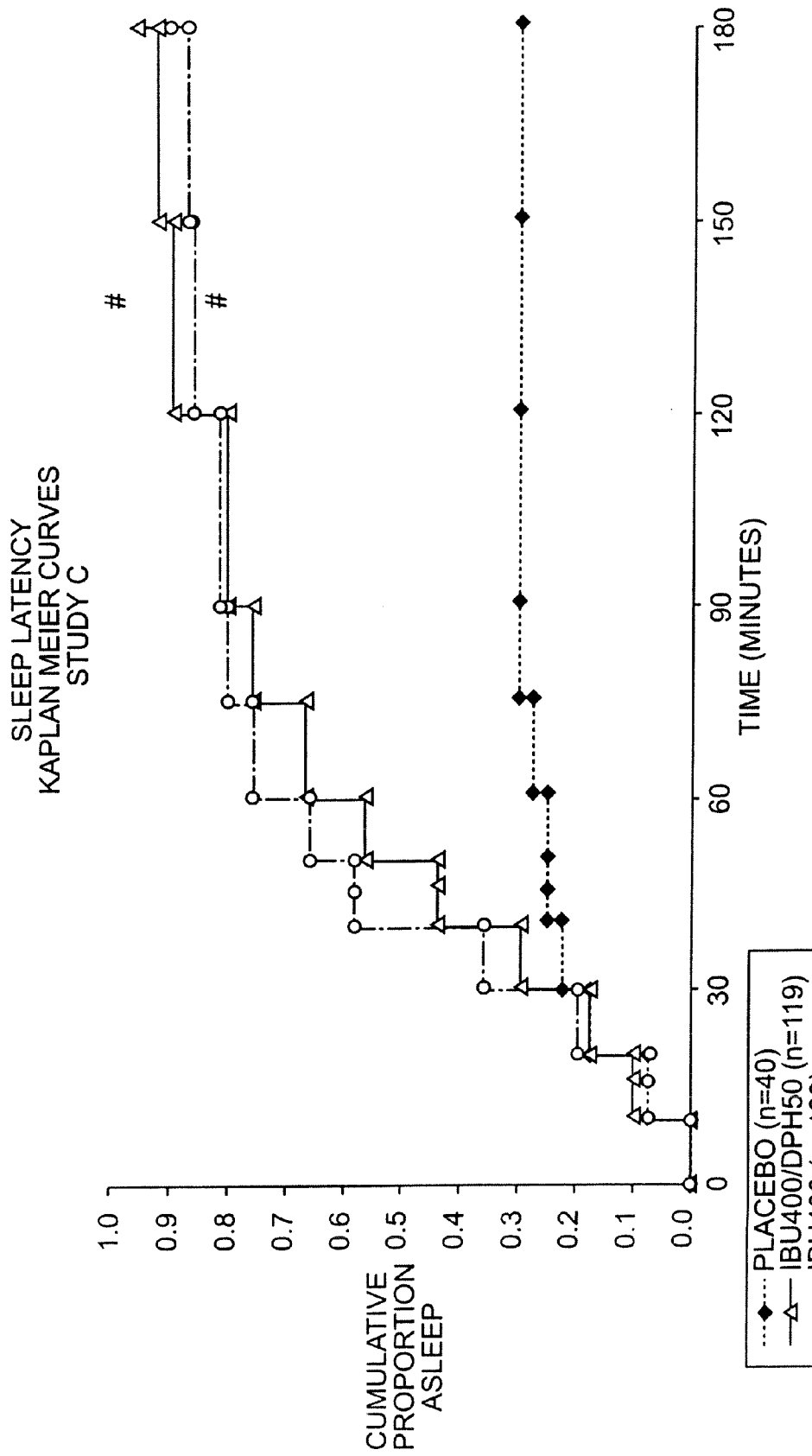
FIG. 17: This figure shows the nurse observed sleep latency data for Study C.
Figure 18:
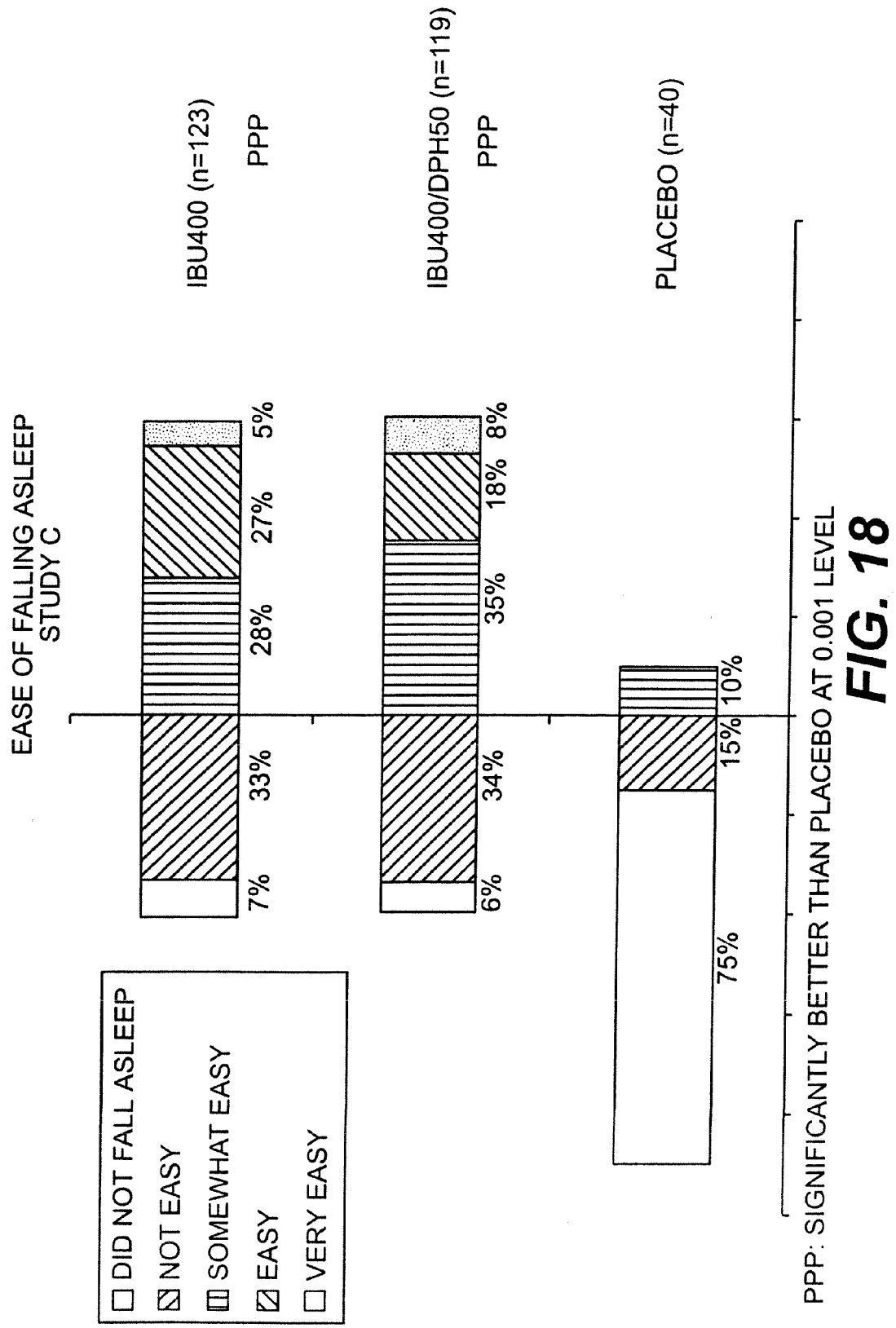
FIG. 18: This figure shows the ease of failing asleep data for Study C.
Figure 19:
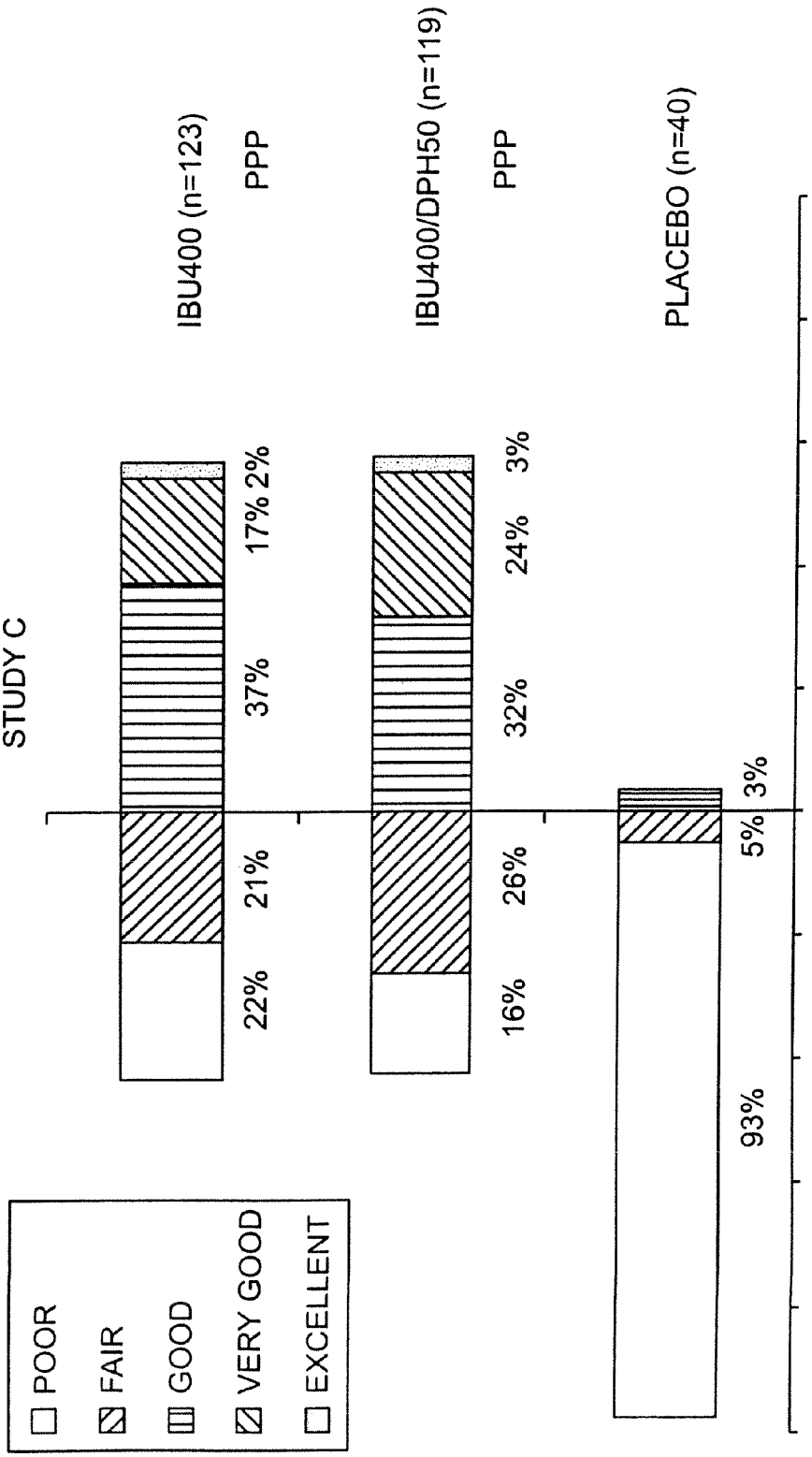
FIG. 19: This figure shows the global evaluation of the study medication as a sleep aid data for Study C.
Figure 20:
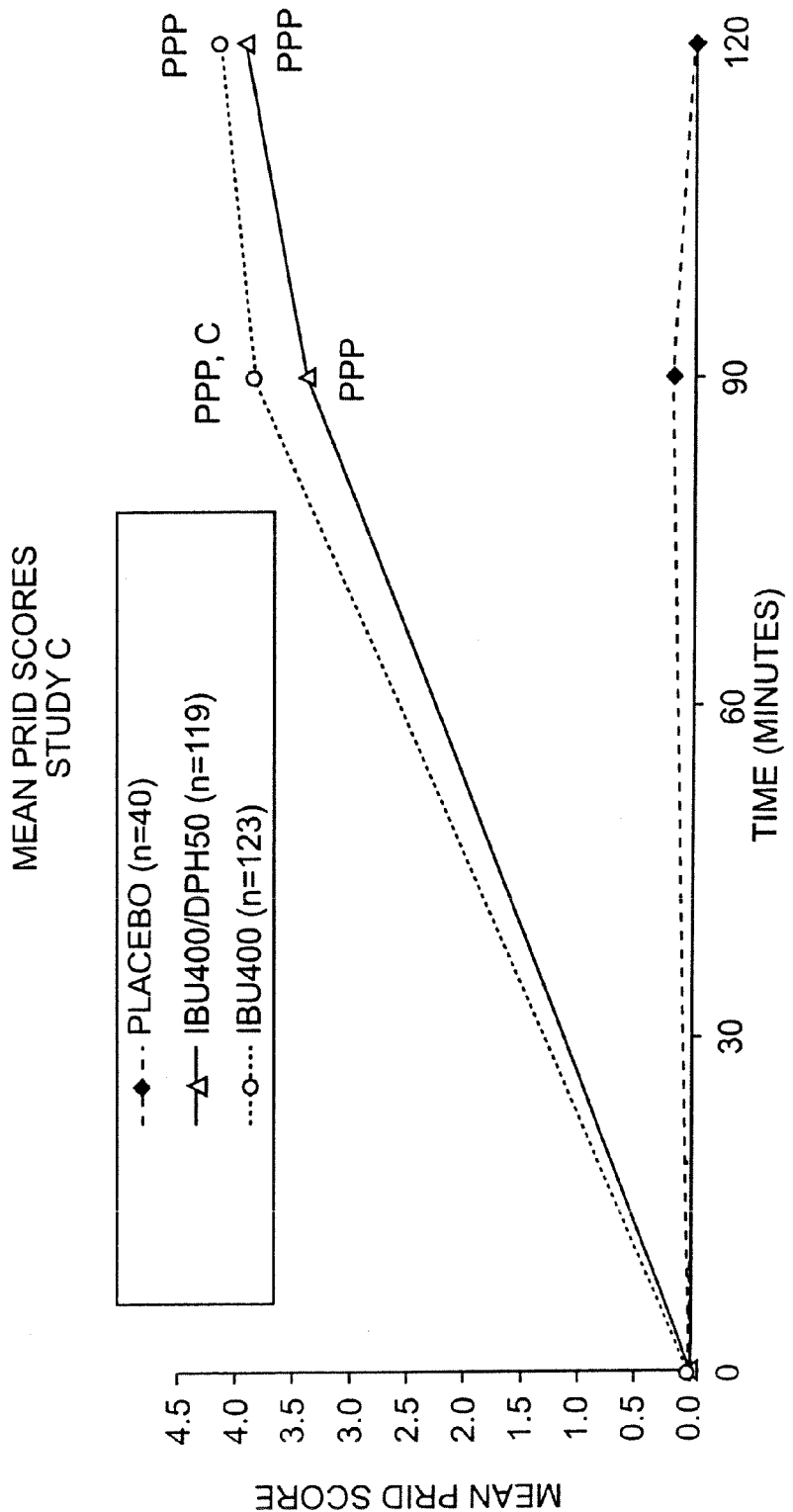
FIG. 20: This figure shows PRID scores for Study C.
Figure 21:
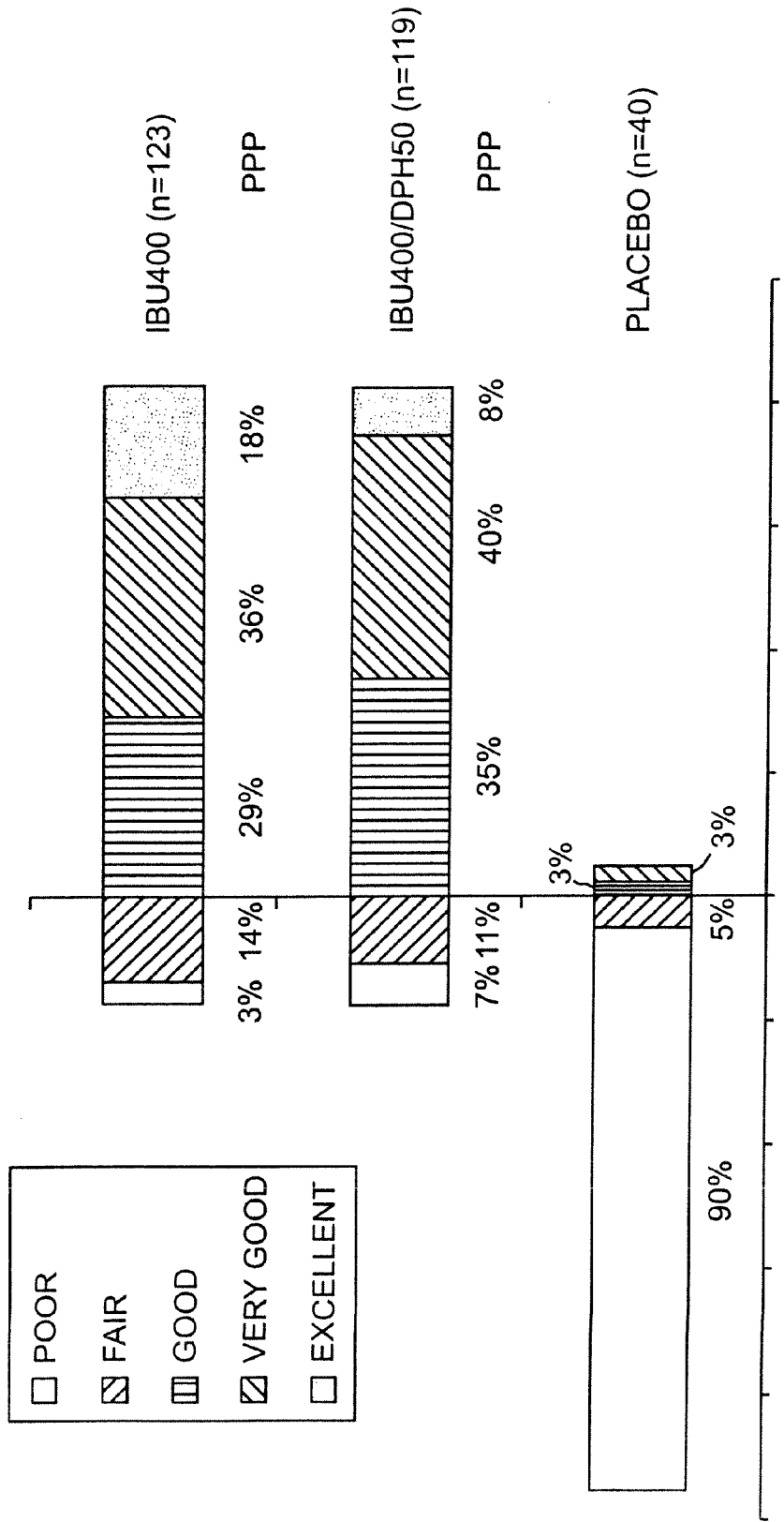
FIG. 21: This figure shows the global evaluation of the study medication as a pain reliever data for Study C.
Figure 22:
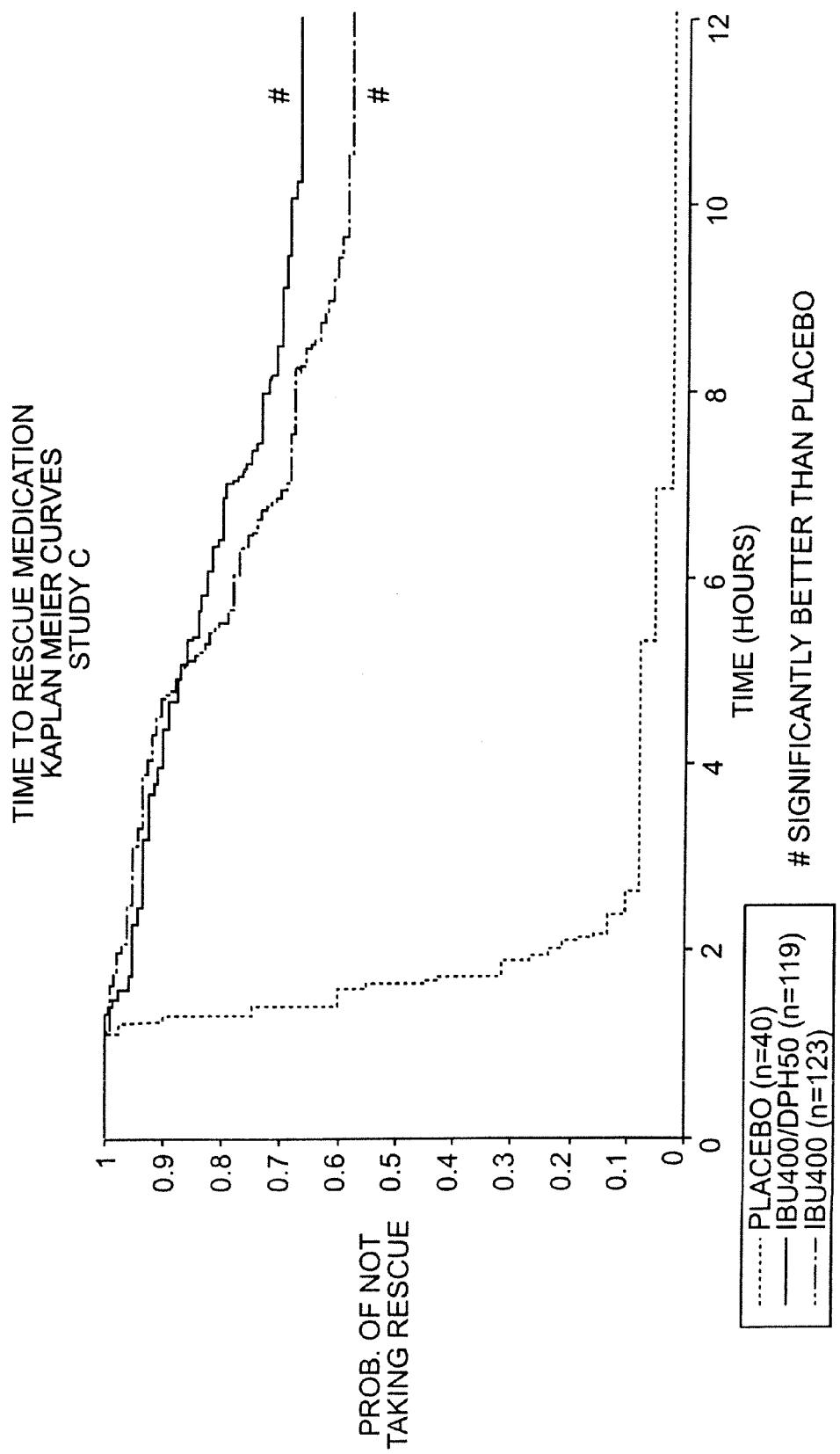
FIG. 22: This figure shows the time to rescue medication for any reason data for Study C.

Applicants have surprisingly discovered that the combination of ibuprofen and diphenhydramine synergistically provides for both an effective pain treatment and an effective treatment for sleep disturbances, including pain-associated disturbances such as shortened sleep duration. The resulting combination yields a somnolent effect which is greater than that which can be attributed to the diphenhydramine alone. This discovery is also surprising because ibuprofen is known to be effective at these doses for only 4 to 6 hours at the doses of the present invention, whereas the observed sleep duration effect from the administration of the composition of the present invention continued for notably longer periods of time. By administration, it is meant that the composition of the present invention can be provided to a patient as ibuprofen and diphenhydramine, or alternatively either or both the ibuprofen or diphenhydramine can be provided to a patient in a prodrug form, which is metabolized in the patient's body into ibuprofen or diphenhydramine, respectively.

Ibuprofen dosages for use in the present invention range from 50 mg to 800 mg, from 100 mg to 800 mg, from 200 mg to 600 mg, from 200 mg to 400 mg, or 200 mg. Diphenhydramine HCl dosages for use in the present invention range from 12.5 mg to 100 mg, from 25 mg to 75 mg, from 25 mg to 50 mg, or 25 mg.

Diphenhydramine citrate can also be used in the present invention, at corresponding levels. For example, 38 mg of diphenhydramine citrate is equivalent to 25 mg diphenhydramine HCl; the correlation between these two compounds is well known in the art. Thus, diphenhydramine citrate dosages for use in the present invention range from 19 mg to 76 mg, from 38 mg to 76 mg, or 38 mg. While precise numbers for the diphenhydramine citrate are provided here and in the claims, it is not intended that these numbers be exact when determining infringement under the doctrine of equivalents. These specific dosages were chosen as they correlate to the amounts provided for the HCl salt of diphenhydramine, according to the differences in molecular weight between the compounds, and reasonable equivalents are still contemplated.

Of course, the dosages can be adjusted to take into account the weight of the patient and the intensity of the pain associated sleep disturbance. For example, higher dosages can be used for a more intense or problematic pain associated sleep disturbance, or for a patient who weighs more than average. Lower doses can be used for a milder problem or for a patient who weighs less than average. Lower doses can also be administered to children, the elderly, or those sensitive to medication.

In the present invention, the desired dose of ibuprofen and diphenhydramine can be included in either in a single pharmaceutical dosage unit (e.g., a tablet or capsule) or can be divided into multiple pharmaceutical dosage units (e.g., the desired doses divided into two or more tablets or capsules). The term dose, thus, means the total amount of an active ingredient given to a patient at one time. Multiple units are considered to be in the same dose if they are given at the same time or within a half an hour period. Additional units given later, such as after the patient continues to suffer from symptoms and realizes the first dose was not sufficient, are considered to be additional doses. One, two or more dosage units may be given, depending upon whether the patient responds to one dosage unit and depending on other factors including the age and size of the patient, and the intensity of the problem for treatment. It is anticipated that the dosages will be such that a patient will typically take one dose, or two doses if needed.

As the ibuprofen and diphenhydramine are administered in a single pharmaceutical composition, steps should be taken to ensure that the ibuprofen and diphenhydramine do not have a chemical interaction with each other. Because ibuprofen has an acidic moiety (—COOH) and diphenhydramine has a basic moiety (—N(CH$_3$)$_2$), it is possible for there to be an acid-base interaction. An ion pair or salt could, thus, be formed. Such an interaction creates a more nonpolar composition, which may have different dissolution characteristics and absorption profile in the body. Such changes in a pharmaceutical composition may be highly undesirable, due to unpredictability of effect. Different forms of diphenhydramine may interact more or less with ibuprofen. Current tests show that the HCl form is much more prone to interaction than the citrate form.

Prior testing on a standard caplet containing the two active ingredients showed evidence of interaction between the diphenhydramine and ibuprofen, including dissolution failures (failure of the active ingredients to dissolve properly when tested under in vitro conditions), appearance problems (mottling and peeling), and potential low potency (active ingredients being lost in the formulation process). Additional testing of a 50:50 composition of diphenhydramine hydrochloride and ibuprofen when taken from a dry to wet (water) state resulted in a transformation from a white powder to a translucent gray sticky mass even after it was dried again, with the change in opacity and color indicating that a chemical interaction had occurred. Furthermore, investigations have shown that when ibuprofen and diphenhydramine powder mixtures are exposed to moisture that changes are observed in the X-ray powder diffraction pattern and the differential scanning calorimetry results. This evidence of a change in the formulation demonstrates that there is a negative interaction that could occur in such a pharmaceutical composition.

The inventive composition may be administered with acceptable pharmaceutical carriers, excipients, or diluents, selected for the intended route of administration and the active ingredients. It is within the skill of one of ordinary skill in the art to identify carriers that are useful for oral administration. These pharmaceutical carriers, excipients, and diluents are listed in the USP pharmaceutical excipients listing. USP and NF Excipients, Listed by Categories, p. 2404-2406, USP 24 NF 19, United States Pharmacopeial Convention Inc., Rockville, Md. (ISBN 1-889788-03-1).

Several beneficial formulations within the scope of the present invention have been created which prevent this undesirable potential chemical interaction between the ibuprofen and diphenhydramine. One formulation is a bilayer tablet or caplet that separates the ibuprofen and diphenhydramine from each other in distinct regions of the tablet or caplet. This physical separation reduces the possibility and/or amount of interaction between the diphenhydramine and ibuprofen.

Another formulation is a PEG-containing soft gelatin capsule (also called "Liquigel™" or "liquid gel"). Surprisingly, the unwanted interaction does not occur in the soft gelatin capsule formulation. While not wishing to be bound by theory, it is currently believed that the PEG in the soft gelatin capsule could reduce the possibility and/or amount interaction, possibly by preferentially interacting with one or both of the active ingredients. PEG 600 can be used in the soft gelatin capsule, as can other formulations such as, but not limited to, PEG 400 and PEG 800.

The bilayer tablet or caplet can be a two layer tablet or caplet that is formed by pressing one half of the tablet or caplet first, and then pressing the second half of the tablet or caplet onto it. Additionally, other separation tablets can be prepared according to the invention. A tablet within a tablet (compression core tablet) can be prepared. Either the ibuprofen or diphenhydramine layer could instead be compressed as a first tablet, with the other layer being compressed on its outside as an outer tablet layer. Furthermore, one of the active ingredients could be incorporated into a coating solution which can be sprayed onto a core tablet or caplet containing the other active ingredient. Either ibuprofen or diphenhydramine could be used in the coating, with the other in the core. Lastly, the particles of one or both drugs could be coated with a suitable barrier material, and then prepared into a tablet or capsule.

One embodiment of a bilayer tablet or caplet contains 200 mg ibuprofen and 38 mg diphenhydramine citrate as the active ingredients. Inactive ingredients may include any of the following calcium stearate, croscarmellose sodium, glyceryl behenate, lactose, microcrystalline cellulose, silicon dioxide colloidal, sodium lauryl sulfate, sodium starch glycolate, corn starch, preglatinized starch, starch, stearic acid, and coloring and ink ingredients. Other inactive tableting ingredients would be recognized by the skilled artisan. This bilayer caplet shows improved dissolution, better appearance, and minimizes any undesired interaction between the active ingredients. This reduces the potential for eutectic formation and liquefaction, which may impact the appearance (causing a mottled, pitted surface), accelerate degradation, and affect dissolution.

One embodiment of the soft gelatin capsule composition contains 200 mg ibuprofen and 25 mg diphenhydramine HCl as the active ingredients. Inactive ingredients may include colors to give the soft gelatin capsule a pleasing appearance (e.g., D&C Red No. 33 and/or FD&C Blue No. 1), gelatin, polyethylene glycol 600 (low aldehyde), potassium hydroxide, purified water USP, ANDRISORB 85/70™ (an aqueous solution of D-sorbitol and sorbitans). Fractionated coconut oil, lecithin, and VM&P naphtha may also used as a processing aid, but do not remain in the soft gelatin capsule to any significant amount in the final formulation because these processing aids are essentially removed during the washing of the final soft gelatin capsule product, prior to bulk packaging.

The skilled artisan understands how to make a soft gelatin capsule, and other formulations would be known to the skilled artisan. See J. P. Stanley, "*Soft Gelatin Capsules,*" *THE THEORY AND PRACTICE OF INDUSTRIAL PHARMACY,* 398-412 (Lachman ed. 3$^{rd}$ ed. 1986); "*Soft Capsules,*" *ENCYCLOPEDIA OF PHARMACEUTICAL TECHNOLOGY,* 269-276 (Swarbrick ed. 1988); "Soft Gelatin Capsules," *PHARMACEUTICAL DOSAGE FORMS & DRUG DELIVERY SYSTEMS,* 176-179 (Ansel ed. 6$^{th}$ ed. 1995).

This composition is usually administered before bedtime in order to have the surprising somnolent effect. The composition can also be administered during the day if the patient wishes to sleep during the day. Often, the composition should be administered from 90 minutes before bedtime to immediately before bedtime. For many applications of the present invention, the composition should be administered from 45 minutes before bedtime to 15 minutes before bedtime. In many case, it has been found that the composition should be administered 30 minutes before bedtime.

One or two dosage units can be taken. If two dosage units are to be taken, they can be taken at the same time, or one dosage unit can be taken with a second dosage unit taken later if needed. The dosage depends on the severity of the condition, the size and age of the patient, and the response of the individual to treatment. In a typical embodiment, each dosage unit may contain 200 mg ibuprofen and 25 mg diphenhydramine HCl (or its equivalent of 38 mg diphenhydramine citrate).

While not wishing to be bound by theory, the beneficial impact of the combination treatment relies on the rapid impact of ibuprofen due to its pharmacokinetic profile, and continuing effects of both the ibuprofen and diphenhydramine. It was surprisingly discovered that ibuprofen continued to have an impact towards the end of the night's sleep, as ibuprofen plasma levels typically drop significantly after 4 to 6 hours.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. The following examples are intended to illustrate the invention without limiting the scope as a result.

EXAMPLES

The following examples illustrate, but are not intended to limit, the scope of the invention.

Example 1

Preparation of an Ibuprofen and Diphenhydramine Soft Gelatin Capsule

The combination soft gelatin capsule was prepared as follows. First, the fill solution was prepared. The potassium hydroxide NF (41.011 kg) was dissolved in water (34.603 kg) with the aid of a Cowels mixer (a large mixing vessel with a propeller-type mixer available from Morehouse-Cowles, Fullerton, Calif.) and was covered. The solution was blanketed with nitrogen while covered. The diphenhydramine hydrochloride (40.050 kg) was dissolved in water (46.138 kg) with the aid of a Cowels mixer. The polyethylene glycol 600 (200.250 kg) was then added with the aid of the Cowels mixer and the mixture was covered. The solution was blanketed with nitrogen while covered.

A Hicks reactor (a propeller-type mixer that operates under negative pressure to minimize air entrapment, available from Hicks Equipment, Louisville, Ky.) was then used. The Hicks reactor was flushed with nitrogen, and then the vacuum on the reactor was pulled. The polyethylene glycol 600 (326.808 kg) was added and the ibuprofen (320.400 kg) was added and mixed under vacuum. The potassium hydroxide solution was added to the ibuprofen dispersion and was mixed under vacuum until uniform. The temperature was maintained between 75 and 125° F.

The diphenhydramine hydrochloride solution was added to the ibuprofen/potassium hydroxide/polyethylene glycol solution in the Hicks Reactor and was mixed under vacuum. The fill solution was allowed to deaerate under vacuum for 15 minutes or more. The Hicks Reactor was pressurized to 10-15 psi and the fill solution was passed through a 77-micron filter into appropriately labeled containers. The containers were covered and blanketed with nitrogen.

Second, the gelatin was prepared. One hundred percent bone gelatin was used; this is preferable to a mixture of bone and skin gelatin because capsules made with pure bone gelatin are less likely to stick together. According to standards established by RP Scherer, Water and ANDRISORB™ were added to a low energy mixing melter, available from Hicks Equipment, Louisville, Ky. The gelatin was vacuum transferred to the melter, while the mixture was slowly agitated and heated under vacuum until melted. The melted gelatin mixture was transferred into a heated stainless steel gel receiver. The coloring agents were added to the melted gelatin solution and blended until uniform using an RP Scherer high speed blender, RP Scherer, St. Petersburg, Fla.

Third, the product was encapsulated. The RP Scherer softgel machine available from RP Scherer, St. Petersburg, Fla. was used to make a gelatin ribbon. The product name was applied to the wet gelatin ribbons by direct transfer of ink from a FLEXO™ plate roll embossed with the product logo. The fill solution was encapsulated within a gelatin shell using a rotary die soft gelatin capsule encapsulation apparatus fitted with a size 12 oval die.

Fourth, the soft gelatin capsules were processed to completion. The soft gelatin capsules were passed through a rotary-tumbler dryer, for 125 minutes at 90° F. and 15-30% relative humidity. The soft gelatin capsules were spread onto shallow drying trays and allowed to air dry for approximately 10 to 14 days. The soft gelatin capsules were then optionally stored in deep holding trays. The softgels were subject to a very short wash with VM&P naphtha using a RP Scherer washer. The soft gelatin capsules were then complete and ready for counting, storage, or final packaging. To retain the color of the capsules, they were kept away from light as much as possible. For example, the capsules can be packaged in opaque blisters.

The final soft gelatin capsule has the following composition per dose.

TABLE 1

Soft Gelatin Capsule Composition

| Ingredient | Amount (mg/dose) |
|---|---|
| Ibuprofen USP | 200 |
| Diphenhydramine HCl USP | 25 |
| D&C Red No. 33 | 0.0113 |
| FD&C Blue No. 1 | 0.0170 |
| Polyethylene Glycol 600 NF, low aldehyde | 329 |
| Potassium Hydroxide NF | 25.6 |
| Purified Water | 50.4 |
| ANDRISORB 85/70 ™ | 93.4 |
| Gelatin NF | 164 |

Example 2

Preparation of an Ibuprofen and Diphenhydramine Bilayer Caplet

The bilayer caplet was prepared as followed. First, the diphenhydramine compression mix was prepared as a dry blend direct compression formulation. Diphenhydramine citrate (59.28 kg), sodium starch glycolate (4.68 kg), FD&C blue #2 color (0.086 kg), Microcrystalline Cellulose NF (EM-COCEL™ 50 M) (94.61 kg), silicon dioxide colloidal (AEROSIL™), and starch pregelatinized 1551 (34.32 kg) were passed through a Kason sifter available from Kason Corp., Millburn, N.J. equipped with a #10 mesh screen into a Diosna P1000. The Diosna P1000 is a high energy mixer and granulator, which is available from Servo-Lift, Rockaway, N.J. These materials were blended for one minute with the rotor on low and chopper on high, followed by the rotor on low for six minutes (no chopper). Glyceryl behenate (COMPRITROL™) (4.69 kg) was passed through a #30 mesh screen and passed into the Diosna bowl through a Kason equipped with a #10 screen. The Diosna was mixed on low speed (rotor only) for three minutes. The contents of the Diosna was then discharged into conical bins, transferred into a FLO-BIN™, available from Flo-Bin, Birmingham, England, and blended for one minute.

Second, the ibuprofen compression mix was manufactured through a wet granulation process. The ibuprofen USP (206 kg), croscarmellose sodium (5.15 kg), starch pregelatinized NF-1551 (19.4 kg), and corn starch NF (81.3 kg) were passed through the Kason sifter equipped with a #4 mesh screen into the Diosna P1000 bowl. The silicon dioxide colloidal NF (AEROSIL™) (1.03 kg) was added to the Diosna bowl and mixed with the rotor and chopper on high for two minutes. The rotor and chopper were set to low, and the granulating liquid (water (115 L)) was added. Following the addition of water, the batch was mixed on low (rotor and chopper) for two minutes, then switched to high (rotor and chopper) until an appropriate end point was reached (2-10 minutes), through visual inspection or by using a power cell. When a power cell was used, the end point was 13% KW change in the power cell reading from the initial KW reading at the onset of high/high granulation.

The wet granulation was discharged from the Diosna and passed through a #4 mesh screen into an AEROMATIC™ T-8 fluid bed bowl and available from Niro Pharmasystems, Columbia, Md., and dried until an appropriate end-point has been achieved (1.5-2.5% moisture content). The dried granulation was then milled through a Frewitt unit equipped with a #16 mesh screen and collected in a 1200 liter FLO-BIN™. Silicon dioxide colloidal NF (AEROSIL 200™) (0.618 kg), sodium lauryl sulfate LX 100 NF (0.495 kg), and starch purity 826 National NF (7.11 kg) were combined, passed through a #30 mesh screen, and transferred to the FLO-BIN™. The croscarmellose sodium (5.10 kg) was added to the FLO-BIN™, which was blended for 20 minutes at 17 RPM. The stearic acid NF powder 1.82 kg was passed through a #30 mesh screen, added to the FLO-BIN™, and blended for four minutes at 17 RPM.

The ibuprofen compression mix and the diphenhydramine compression mix were then compressed together as bilayer caplets, each layer containing an individual active ingredient. The ibuprofen layer (318.6 mg total weight per dose) was compressed as the first layer, while the diphenhydramine layer (220 mg total weight per dose) was compressed as the second layer. The caplets were compressed on a Manesty Mark IIA bilayer press, with the following parameters:
tooling (shape of caplet punch) 0.590"×0.283"×0.045";
press speed: 1200-1600 TPM;
ibuprofen layer thickness 0.173" to 0.185"; and
bilayer thickness (of the whole bilayer caplet) 0.226" to 0.234".

The uncoated cores are then transferred to a 67" Vector Hi-Coater, where a 5% Opadry II Blue coating is applied under the following conditions:
Warmup: pan speed=5.5 RPM
air inlet temperature=155° F.
jog the pan until exhaust temperature reaches 115° F. stabilized
Cycle #1 inlet air temperature=162° F.
pan speed=5.0 RPM
spray rate=160 mL/min
spray time=60 minutes
Cycle #2 inlet air temperature=162° F.
pan speed=6.0 RPM
spray rate=160 mL/min
spray time=to end of coating (as measured by a predetermined weight gain)

Following the coating process the tablets were dusted with calcium stearate, discharged from the Hi-Coater.

The final bilayer caplet had the following composition per dose:

TABLE 2

Caplet Composition

| Ingredient | Amount (mg/dose) |
|---|---|
| Ibuprofen USP | 200 |
| Diphenhydramine Citrate USP | 38 |
| Calcium Stearate | 0.0050 |
| Croscarmellose Sodium | 10.0 |
| Glyceryl Behenate NF | 3.00 |
| Lactose NF, Monhydrate Spray Dried | 90.0 |
| Microcrystalline Cellulose NF (EMCOCEL ™ 50 M) | 60.6 |
| Silicon Dioxide Colloidal NF AEROSIL 200 | 4.90 |
| Sodium Lauryl Sulfate LX100 NF | 0.500 |
| Sodium Starch Glycolate NF | 3.00 |
| Starch Corn | 78.9 |
| Starch Pregelatinized NF-1551 | 40.8 |
| Starch Purity 826 Nat'l NF | 7.00 |
| Stearic Acid NF, Powder, Food Grade | 1.80 |
| FD&C Blue #2 Alum. Lake 35%-42% | 0.0550 |
| Opadry II Blue 49B10882 | 26.9 |

Example 3

Comparison of Ibuprofen, Diphenhydramine, and Ibuprofen/Diphenhydramine Combination (Study A)

105 patients were evaluated for sleep disturbances after oral surgery. At baseline, 60% of the subjects had moderate levels of pain, while 40% had severe pain. A single center, inpatient, single dose, randomized (stratified by gender and baseline pain severity), double blind, double dummy, parallel group placebo controlled study was used.

In a double dummy scenario, patients are given multiple dosage forms, one study medication for the group in which they are assigned, and placebos resembling the dosage forms for the other study groups. Thus, even though the dosage forms for the various treatment groups looked different, the patients were not able to ascertain to which group they were assigned. 14 patients were assigned to the placebo group, 29 to the ibuprofen/diphenhydramine combination group, and 31 each in ibuprofen and diphenhydramine groups. The ibuprofen dose was 400 mg and the diphenhydramine HCl dose was 50 mg. The combination was in a soft gelatin capsule formulation.

Patients were evaluated using the following parameters:
sleep latency (time it takes to go to sleep as evaluated by a nurse),
SPRID3 (time-weighted sum of pain relief and pain intensity differences from baseline over 0-3 hours),
cumulative percent asleep at 60 minutes (nurse graded),
ease of falling asleep (assessed by the patient at the time of rescue medication, if needed, or in the morning, if no rescue medication, using a 5-point categorical scale: 0=did not fall asleep to 4=very easy to fall asleep),
duration of sleep (assessed by the patient at the time of rescue medication, if needed, or in the morning, if no rescue medication, using a 6-point categorical scale: 0≦5 hours, 1=5-6 hours, 2=6 to <7 hours, 3=7 to <8 hours, 4=8 to <9 hours, 5≧9 hours).
global evaluation of sleep (assessed by patient at the time of rescue medication, if needed, or in the morning, if no rescue medication, using a 5-point categorical scale: 0=poor to 5=excellent),
median time to rescue medication (nurse recorded, in hours), and
and percent of patients requiring rescue medication.

The art recognizes that patient-assessed duration of sleep is a very good indicator of the amount of sleep received by the patient. If patients requested rescue medication within an hour of receiving treatment, they were considered protocol violators and removed from the study.

The SPRID3 calculation was as follows. AT 90 minutes, 2 hours, and 3 hours, the patients were woken and asked two questions: how much relief of pain have you had? (no relief=0, a little=1, some=2, a lot=3, complete=4) and what is the severity of your pain? (none=0, mild=1, moderate=2, severe=3). Pain intensity difference (PID) was determined by subtracting the severity of pain score at the time in question to the baseline score measured before treatment. The pain relief rating (PPR) was then added to the PID for a PRID score. The PRID scores were plotted on a graph over time for each patient, and the SPRID3 score was read as the area under the curve for each patient's PRID plot. SPRID3 is a combination measurement of pain relief and pain severity.

Sleep latency and SPRID3 were the primary parameters in this study. The results are presented in Table 3, with graphical representations of the data in FIGS. 1-4.

TABLE 3

Efficacy Results

| | Placebo | DPH | IBU | IBU/DPH |
|---|---|---|---|---|
| Sleep Latency (median) | 30.0[1] A | 51.3 A | 25.0 B | 36.3 B |
| SPRID3 | 0.9 A | 1.8 A | 13.7 B | 12.8 B |
| Cumulative % Asleep at 60 minutes | 57.1 A | 61.3 A | 77.4 AB | 89.7 B |
| Ease of Falling Asleep | 0.71 A | 1.06 A | 2.10 B | 2.14 B |
| Duration of Sleep | 0.36 A | 0.23 A | 2.68 B | 3.31 B |
| Global Evaluation | 0.64 A | 0.77 A | 1.84 B | 2.17 B |
| Time to Rescue (median) | 1.20 A | 2.04 A | >10 B | >10 B |
| % Requiring Rescue | 93% A | 97% B | 45% B | 48% B |

[1]Although 50% of the subjects in the placebo group fell asleep by 30 minutes, of the remaining only one fell asleep. The A and B designations refer to statistical significance evaluations. All values marked B are statistically significantly different from all values marked A. The value marked AB is not statistically significant from the any of the values marked A or B.

The ibuprofen/diphenhydramine combination group showed improvement over all the other groups for cumulative percent asleep at 60 minutes, ease of falling asleep, duration of sleep, and global evaluation. The results for duration of sleep were surprising because the combination showed a synergistic effect, resulting in scores higher than the combined scores of diphenhydramine and ibuprofen. However, the differences between the ibuprofen/diphenhydramine group and the ibuprofen group alone were not significant, probably due to the sample size.

In this model, only one hour of phase shifting sleeplessness was induced, compared to three hours in subsequent studies. In other words, patients were required to go to sleep one hour earlier than their bedtime. Thus, this study did not have as much sleeplessness as later studies. This may account, in part, for random, nonsignificant variation in the sleep latency and SPRID3 parameters. Additionally, because of the pharmacokinetic profile of diphenhydramine, it was not expected to have a significant effect on the parameters evaluating the impact of the combination soon after treatment. On average, diphenhydramine does not reach effective concentrations in the plasma until 2 hours after treatment. Thus, it was not expected to have an impact on SPRID3 and sleep latency, which evaluate sleep and pain soon after treatment.

Example 4

Comparison of Ibuprofen/Diphenhydramine Combination to Ibuprofen Alone and Placebo (Study B)

This study was conducted in a similar manner to Example 1. The diphenhydramine group was omitted, because, as Example 1 demonstrated, it did not provide adequate treatment for study purposes, especially as the patients were experiencing post-surgical pain. Additionally, the effects of diphenhydramine on sleep are known and do not require further study.

The combination group received a total dose of 400 mg ibuprofen and 50 mg diphenhydramine in a two combination soft gelatin capsules. The ibuprofen group received 400 mg total dose in two soft gelatin capsules. The placebo group also received soft gelatin capsules.

The trial was conducted as a randomized, stratified (by baseline pain and gender), inpatient, placebo controlled, partial factorial, single dose, double blind, parallel group, single center trial. Following oral surgery, patients were kept at the clinic site overnight. Study medications were dispenses when patients experienced pain at a moderate level or greater, and when it was between about 6:30 and 8:00 p.m. (3 hours prior to the patient's usual bedtime). Patients were required to go to sleep after receiving study medication.

The same sleep parameters were used as in Example 1. Additionally, global assessment as a pain reliever was determined. This parameter was a patient-assessed parameter made at the time of rescue medication, if needed, or in the morning, if no rescue medication. Pain relief was assessed on a five-point scale (0=poor, 1=fair, 2=good, 3=very good, 4=excellent). Sleep was monitored by an observer at regular intervals over 3 hours post-dosing. Patients provided pain assessments at 90 and 120 minutes post-dosing. Patients also provided subjective assessments of sleep efficacy, global assessments of sleep and pain the next morning or at the time rescue medication was used.

The following statistical methods were used. All analyses were done using SAS® Version 6.12. Subjective sleep and pain assessments were analyzed by analysis of variance (ANOVA), incorporating effects for treatment, baseline pain severity rating (PSR), and gender in the model. In addition, the interactions of treatment-by-baseline PSR and treatment-by-gender were assessed (at the 0.15 level) in separate models, by adding interaction terms, one at a time, to the initial ANOVA model. The distributions of sleep latency and time to rescue medication were assessed using the Kaplan-Meier estimates, and the variables were analyzed using the Cox proportional hazards regression model with treatment, baseline PSR and gender effects. In addition, the interactions of treatment-by-baseline PSR and treatment-by-gender were assessed (at the 0.15 level) in separate models by adding each interaction term, one at a time, to the initial model.

If each interaction was generally significant (p≦0.15), it was retained in the final model. In the assessment of treatment effects in the presence of interactions, each level of the stratifying variable were to be weighted equally (consistent with the ANOVA models). Ninety-five percent confidence intervals for the median time to sleep and median time to rescue medication were derived. In addition, the actual and cumulative proportion of subjects asleep at each observation time point and the cumulative proportion of subjects who took rescue medication by each observation time point were analyzed by the Cochran-Mantel-Haenszel test controlling for baseline PSR and gender.

In order to protect the Type I error at the 0.05 level, comparisons were tested in sequential order. Each step had to be significant for the subsequent steps to be eligible for significance. The sequential order used was as follows:

Ibuprofen 400 mg/diphenhydramine hydrochloride 50 mg vs. placebo: in order to be eligible for being declared significant, each of the primary sleep and pain parameters had to be significant at the 0.05 level;

Ibuprofen 400 mg/diphenhydramine hydrochloride 50 mg vs. ibuprofen 400 mg: in order to be eligible for being declared significant the primary sleep parameter had to be significant at the 0.05 level; and Ibuprofen 400 mg vs. placebo: in order to be eligible for being declared significant the primary pain parameter had to be significant at the 0.05 level.

The secondary end points were assessed at the 0.05 level of significance, in the same sequential order.

The primary analysis of efficacy was conducted on the intent-to-treat population, which included all randomized subjects who took the study medication and had at least one post-baseline (sleep and pain) efficacy assessment.

204 patients (72.9%) rated their baseline pain severity as "moderate" and 76 (27.1%) as "severe." The treatment groups were comparable with respect to baseline pain severity.

Results for the study are shown in Table 4, with graphical representations of the data in FIGS. 5-12.

TABLE 4

Efficacy Results

| Parameter | Placebo (n = 40) | IBU 400 mg/ DPH 50 mg (n = 122) | IBU 400 mg (n = 118) |
|---|---|---|---|
| Cumulative % Asleep at 60 minutes | 40.0 | 63.9† | 64.4† |
| SPRID2 | 1.33 | 7.67* | 7.63* |
| Sleep Latency (Observed) - median (minutes) | >180 | 42.9* | 44.0* |
| Ease of Falling Asleep$^a$ - mean | 0.85 | 1.91* | 1.81* |
| Duration of Sleep$^b$ - mean | 0.28 | 2.81*§ | 2.26* |
| Global Assessment as a Sleep-Aid$^c$ | 0.53 | 1.76* | 1.63* |
| PRID 90 minutes | 0.71 | 3.79* | 3.72* |
| PRID 120 minutes | 0.53 | 3.96* | 4.09* |
| Global Assessment as a Pain Reliever$^c$ | 0.68 | 2.32* | 2.30* |
| Time to Rescue Medication for Any Reason (hours) | 1.7 | >12* | >12* |
| % Requiring Rescue Medication for Any Reason | 85 | 36.9*ζ | 48.3* |

DPH = diphenhydramine,
IBU = ibuprofen
*p ≦ 0.001 vs. placebo
†p ≦ 0.01 vs. placebo
§p ≦ 0.05 vs. IBU 400 mg
ζ0.05 < p ≦ 0.10 v. IBU 400 mg
$^a$Assessed using a 5-point categorical scale (0 = didn't fall asleep to 4 = very easy to fall asleep)
$^b$Assessed using a 6-point categorical scale (p = <5 hours, 1 = 5-6 hours, 2 = 6+-7 hours, 3 = 7+-8 hours, 4 = 8+-9 hours, 5 = >9 hours)
$^c$Assessed on a 5-point categorical scale (0 = poor to 4 = excellent)

The combination was better than ibuprofen alone for most sleep assessment parameters. This difference was statistically significant for duration of sleep and marginally significant for percent requiring rescue medication. The combination allowed patients to sleep significantly longer, providing an important improvement in therapy. It was surprising that ibuprofen impacted sleep at the end of the night, i.e., duration of sleep, because its plasma levels fall after 4 to 6 hours. Again, cumulative percent asleep measured the effect of the drug early in the night, and due to diphenhydramine's slower pharmacokinetic profile, the combination group was no better than the ibuprofen group. A graphical representation of these data are shown in FIGS. 4-12.

Example 5

Comparison of Ibuprofen/Diphenhydramine Combination to Ibuprofen Alone (Study C)

This study was designed to evaluate the analgesic and sedative efficacy of ibuprofen/diphenhydramine soft gelatin capsules containing a total dose of 400 mg ibuprofen and 50 mg diphenhydramine hydrochloride. The ibuprofen only group received a total dose of 400 mg in soft gelatin capsule form.

This was a randomized stratified (by baseline pain and gender), inpatient, placebo-controlled, partial-factorial, single-dose, double-blind, parallel group, single-center trial. Following oral surgery, subjects were housed and observed at a clinic site overnight. When subjects experienced at least moderate pain and it was between approximately 6:30 PM and 8:00 PM (at least 3 hours earlier than their usual bedtime), they received study medication and were required to go to bed for the evening. Sleep was evaluated by an observer at regular intervals over 3 hours post-dosing. Subjects provided pain assessments at 90 and 120 minutes post-dosing. Subjects also provided subjective assessments of sleep efficacy as well as global assessments of the study medication as a sleep-aid and as an analgesic the next morning (or at the time rescue medication was used).

The patients were assessed for duration of sleep, cumulative percent of subjects asleep at 60 minutes post-dosing (based on observed sleep latency assessments). they were also assessed for pain using SPRID2 (time-weighted sum of pain relief and pain intensity differences from baseline over 0-2 hours). Sleep latency (observer based), ease of falling asleep, and global evaluation of sleep were also used. Pain intensity difference combined with pain relief scores (PRID) at 90 and 120 minutes post-dosing, and global-evaluation of the study medication as a pain reliever, as well as time to rescue medication were assessed.

All analyses were done using SAS® Version 6.12. Cumulative percent of subjects asleep by 60 minutes was analyzed by the Cochran-Mantel-Haenszel test controlling for baseline PSR and gender. Subjective sleep and pain assessments were analyzed by analysis of variance (ANOVA), incorporating effects for treatment, baseline pain severity rating (PSR), and gender in the model. The distributions of sleep latency and time to rescue medication were assessed using the Kaplan-Meier estimates, and the variables were analyzed using the Cox proportional hazards (PH) regression model with treatment, baseline PSR, and gender effects. For both ANOVA and PH models, the interactions of treatment-by-baseline PSR and treatment-by-gender were assessed (at the 0.15 level) in separate models by adding each interaction term, one at a time, to the initial model. If each interaction was generally significant ($p \leq 0.15$), it was retained in the final model. In the assessment of treatment effects in the presence of interactions, each level of the stratifying variable was to be weighted equally.

In order to protect the Type I error at the 0.05 level, comparisons were tested in sequential order for the primary as well as the secondary efficacy endpoints. Each step had to be significant for the subsequent steps to be eligible for significance. The sequential order used was as follows:

Ibuprofen 400 mg/diphenhydramine hydrochloride 50 mg vs. placebo: in order to be eligible for being declared significant, both primary sleep parameters and the primary pain parameter and has to be significant at the 0.05 level;

Ibuprofen 400 mg/diphenhydramine hydrochloride 50 mg vs. ibuprofen 400 mg: Duration of sleep was tested first followed by cumulative percentage of subjects asleep at 60 minutes, each at the 0.05 level. The cumulative percentage of subjects asleep at 60 minutes was eligible for being declared significant only if the duration of sleep was significant as it protects the alpha error at the 0.05 level of significance.

Ibuprofen 400 mg. vs. placebo: in order to be eligible for being declared significant, the primary pain parameter had to be significant at the 0.05 level.

The secondary end points were assessed, at the 0.05 level of significance, in a similar sequential order. The primary analysis of efficacy was based on the intent-to-treat (ITT) population, which included all randomized subjects who took study medication and had at least one post-baseline (sleep and pain) efficacy assessment.

At the beginning of the study, 164 (58%) patients of the subjects had "moderate" baseline pain severity and 118 (42%) rated their baseline pain as "severe." The mean baseline visual analog scale score was 76.5 mm. The treatment groups were comparable with respect to both measures of baseline pain severity.

The results of this study can be found in Table 5, with graphical representations in FIGS. 13-22.

TABLE 5

Efficacy Results

| Parameter | Placebo (n = 40) | IBU 400 mg/DPH 50 mg (N = 119) | IBU 400 mg (N = 123) |
|---|---|---|---|
| Duration of Sleep[a] | 0.05 | 2.61[†*] | 1.98[†] |
| Cumulative % Asleep at 60 minutes | 27.5 | 66.4[†] | 75.6[†] |
| SPRID2 | 0.26 | 7.03[†] | 7.81[†,§] |
| Sleep Latency (Observer) - median (minutes) | >180 | 45.0[†] | 36.5[†] |
| Ease of Falling Asleep[b] | 0.35 | 1.87[†] | 1.89[†] |
| Global Assessment as a Sleep-Aid[c] | 0.10 | 1.71[†] | 1.57[†] |
| PRID 90 minutes | 0.18 | 3.39[†] | 3.83[†,§] |
| PRID 120 minutes | 0.00 | 3.91[†] | 4.13[†] |
| Global Assessment as a Pain Reliever[c] | 0.18 | 2.30[†] | 2.51[†] |
| Time to Rescue Medication for Any Reason (hours) | 1.6 | >12[†] | >12[†] |
| % Requiring Rescue Medication for Any Reason | 95 | 33.6[†] | 42.3[†] |

[†]$p \leq 0.001$ vs. placebo
[*]$p \leq 0.005$ vs IBU 400 mg
[§]$p \leq 0.05$ vs. IBU 400 mg/DPH 50 mg
[a]Assessed using a 6-point categorical scale (0 = <5 hours, 1 = 5-6 hours, 2 = 6+-7 hours, 3 = 7+-8 hours, 4 = 8+-9 hours, 5 = >9 hours)
[b]Assessed using a 5-point categorical scale (0 = didn't fall asleep to 4 = very easy to fall asleep)
[c]Assessed on a 5-point categorical scale (0 = poor to 4 = excellent)

The combination of ibuprofen and diphenhydramine was statistically superior to ibuprofen alone for duration of sleep, and better for global assessment of the study medication as a sleep-aid and for the percent requiring rescue medication. The combination, again, allows patients to sleep significantly longer than ibuprofen alone. The combination may have been worse for pain treatment because the single-entity soft gelatin capsule has faster release/absorption pharmacokinetics. The absorption profile for the combination is different from the single-entity ibuprofen soft gelatin capsule.

Example 6

Comparison of Different Doses in the Combination (Study D)

This study was designed to evaluate the sedative and analgesic efficacy of 200 mg ibuprofen and 25 mg diphenhydramine (1 soft gelatin capsule dose or single dose) versus 400 mg ibuprofen and 50 mg diphenhydramine (2 soft gelatin capsule dose or double dose).

This study was a single center, in patient, single dose, randomized (stratified by gender and baseline pain severity), double blind, parallel group, placebo controlled dose-response study. Subjects had undergone oral surgery and were housed at the clinic site overnight. They were required to go to bed at least 3 hours earlier than usual. Each active drug versus placebo was assigned in the ratio of 3:3:1. The 284 patients were assigned to the following groups: 41 to placebo, 120 to the single dose, and 123 to the double dose. The treatment groups were also comparable with respect to the surgical procedure characteristics, except for the trauma rating: there was a higher percentage of subjects who received a double does whose trauma was "severe" compared to the other groups (35.8% vs. ~22%). Approximately 59% of the subjects had moderate baseline pain, while 41% were severe.

The results of this study can be found in Table 6, with graphical representations in FIGS. 23-27.

TABLE 6

Single Dose vs. Double Dose

| | Placebo n = 41 | Single Dose n = 120 | Double Dose n = 123 |
|---|---|---|---|
| Duration of Sleep | 0.56 | 2.55† | 3.10†§ |
| Cumulative % Asleep at 60 minutes | 48.8% | 86.7% | 88.6% |
| Nurse observed sleep latency | 63.8 | 31.8† | 30.8† |
| Ease of falling asleep | 0.90 | 2.03† | 2.19† |
| SPRID2 | 1.7 | 8.2† | 9.2†* |
| TOTPAR | 1.39 | 5.31 | 5.94† |
| PRID 90 min | 0.90 | 4.06† | 4.54†£ |
| Global assessment as a sleep aid | 0.56 | 2.10† | 2.25† |
| Global assessment as a pain reliever | 0.51 | 2.44† | 2.73† |

Figure 23:
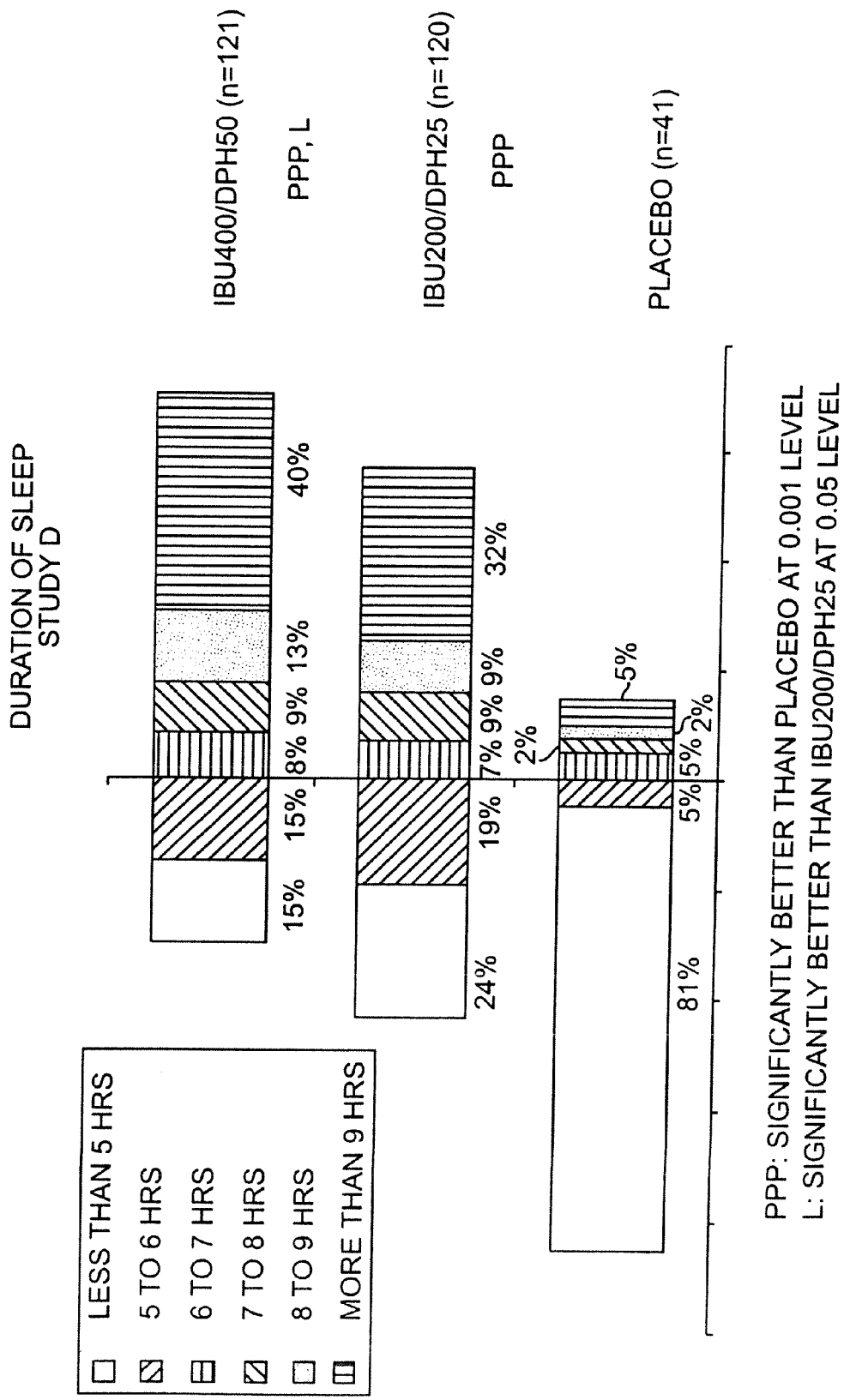
FIG. 23: This figure shows the duration of sleep data for Study D.
Figure 24:
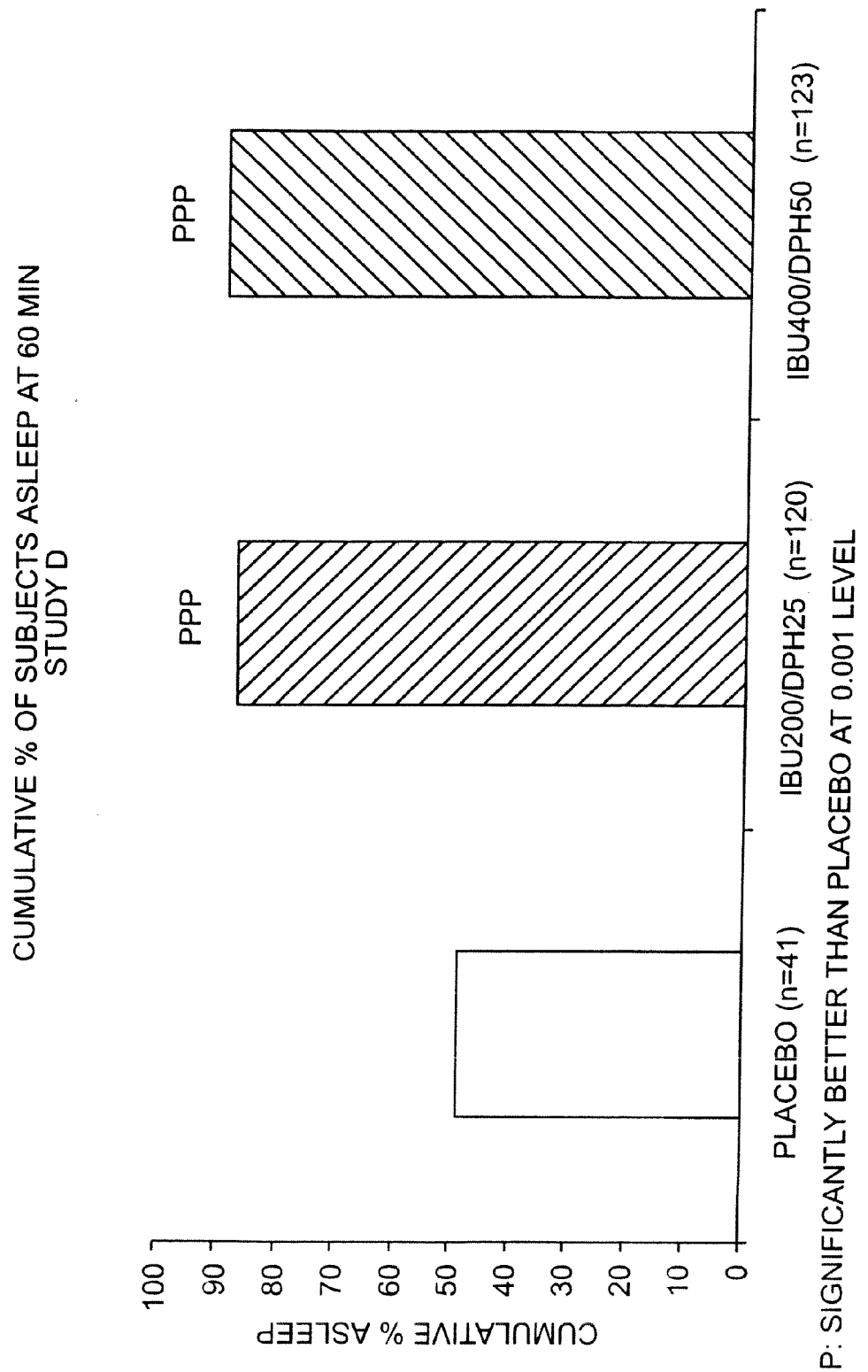
FIG. 24: This figure shows the cumulative percent of subjects asleep by 60 minutes for Study D.
Figure 25:
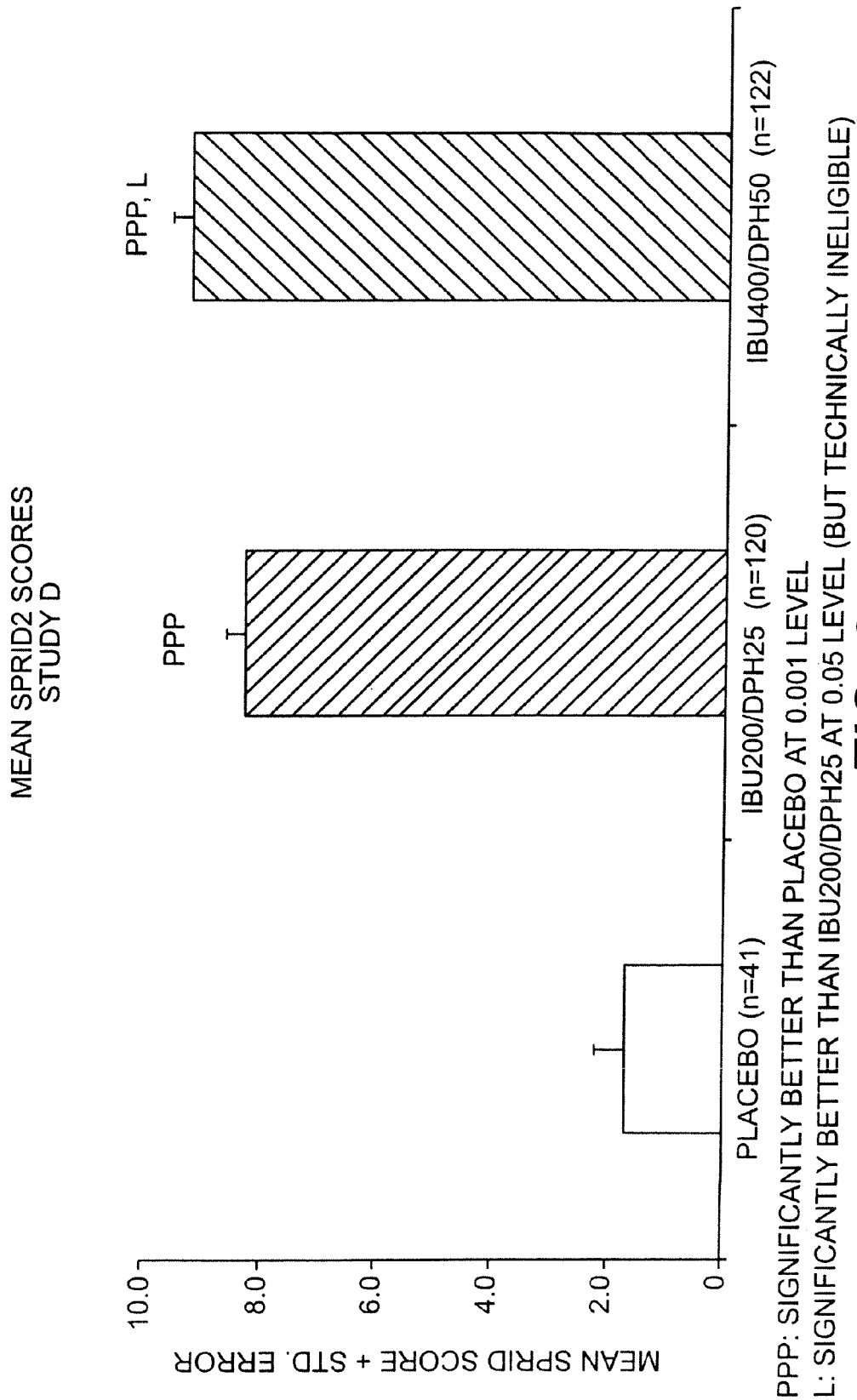
FIG. 25: This figure shows the mean SPRID2 scores for Study D.
Figure 26:
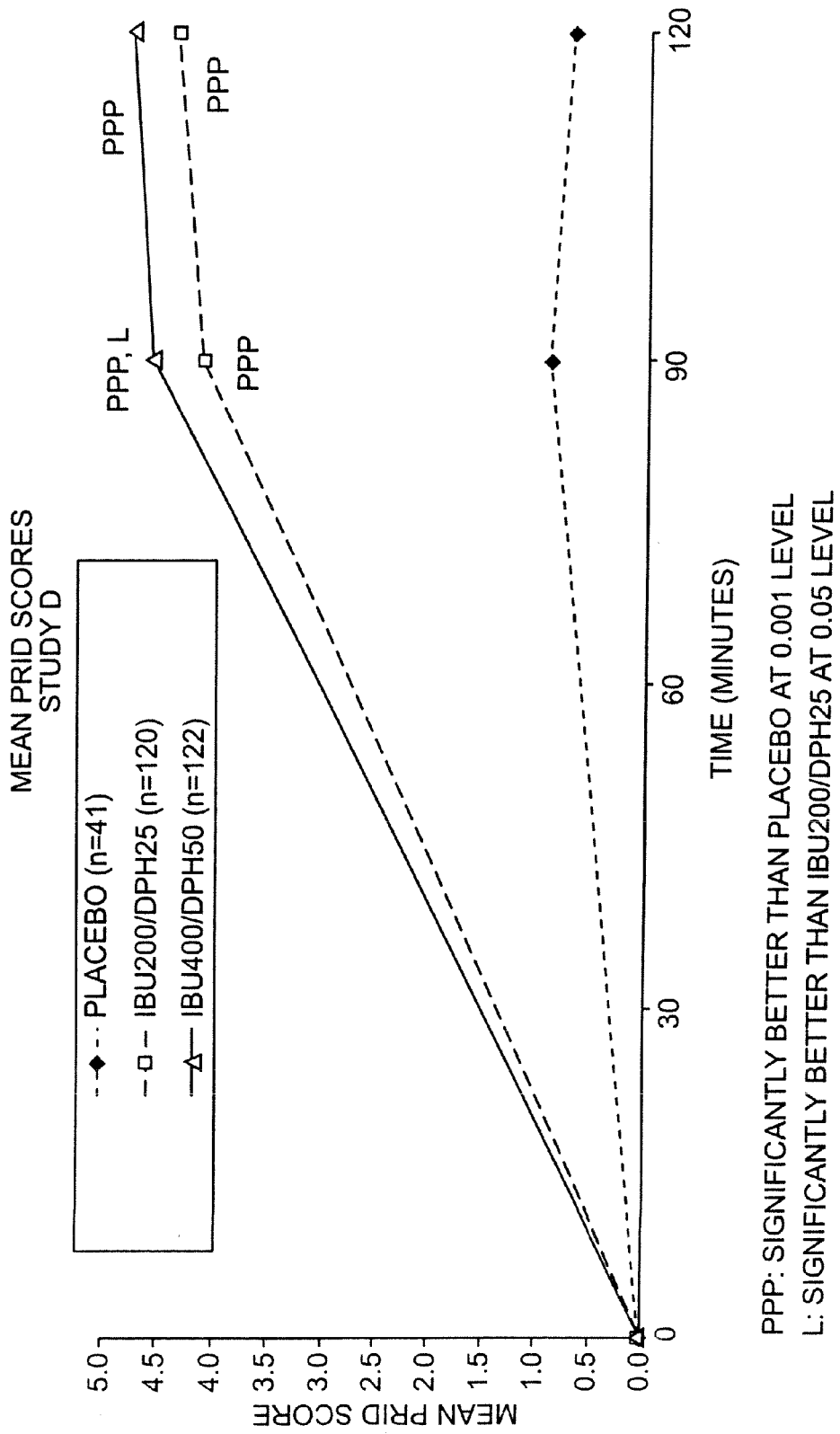
FIG. 26: This figure shows another representation of the SPRID2 scores for Study D.
Figure 27:
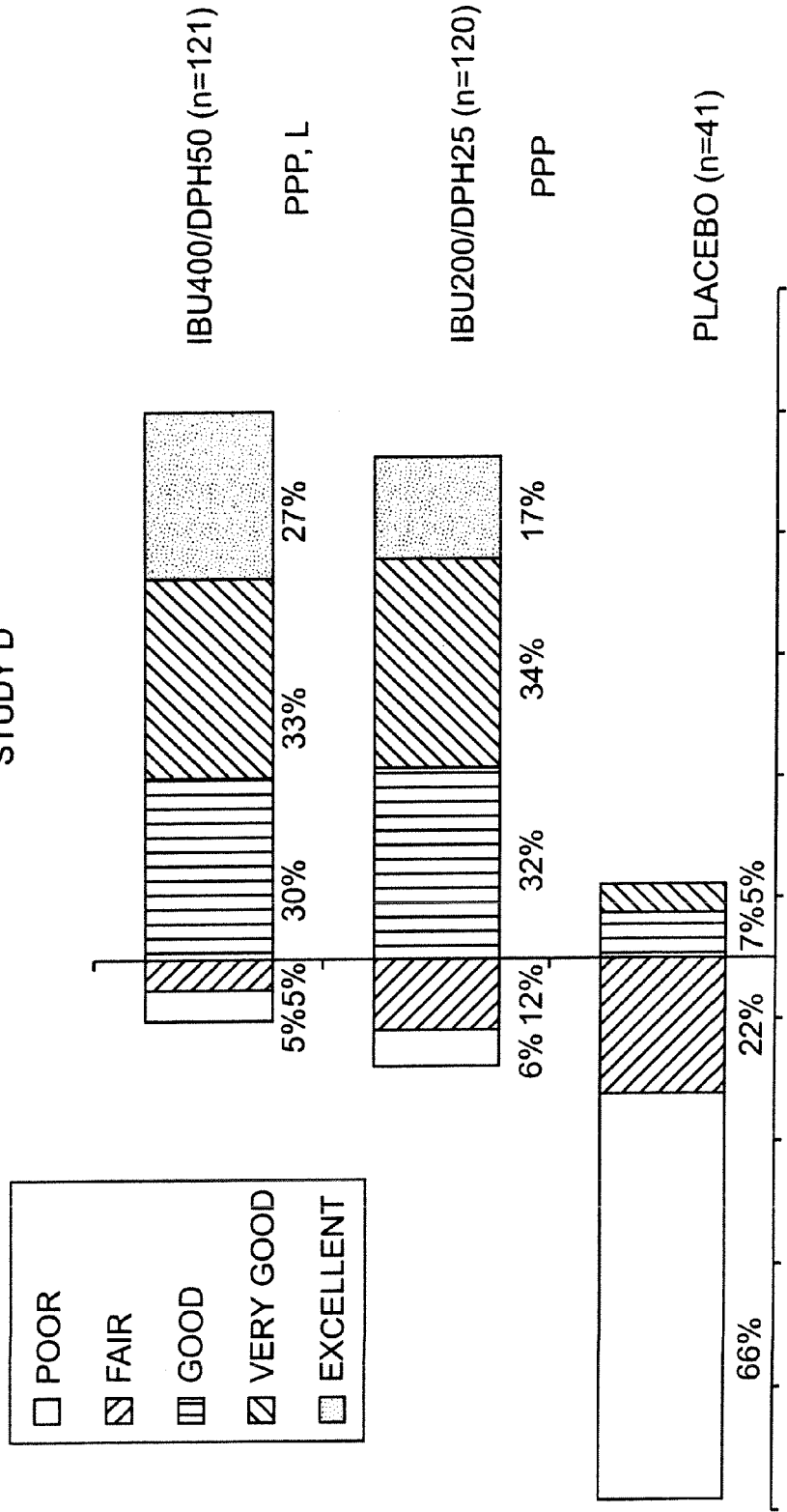
FIG. 27: This figure shows the mean PRID scores over time for Study D.

†Significantly better than placebo
*p = 0.042 when double dose compared to single dose
§p = 0.025 when double dose is compared to single dose
£p = 0.038 when double dose is compared The double dose was better at promoting sleep and treating pain than the single dose although not statistically significantly different. The double dose was significantly better than the single dose for duration of sleep (FIG. 23). By 60 minutes, 48%, 86.7%, and 88.6% of the subjects in the placebo, single dose, and double dose groups were asleep (FIG. 24). The SPRID2 scores in the same groups were 1.7, 8.2, and 9.2, respectively (FIG. 25). At 90 minutes the PRID scores were significantly better for the double dose group (FIG. 26). TOTPAR is an assessment of pain relief: PRR scores were plotted over time, and the area under the curve was determined.

This study shows that higher doses provide significantly more pain relief than the lower doses (FIG. 27) and allow patients to sleep for a longer period of time.

Example 7

Comparison of Study Results

Data from two of the studies were pooled together. Some of the most significant study data are presented in Table 7, with graphical representations of the data in FIGS. 28-29.

TABLE 7

Sleep parameters in Partial Factorial Studies Showing Advantage of IBU/DPH vs IBU Subjects

| Parameter Study | PBO | IBU | IBU/DPH |
|---|---|---|---|
| Duration of Sleep[1] | | | |
| Study AE-98-01 | 0.28 A | 2.26 B | 2.81 C |
| Study AE-98-02 | 0.05 A | 1.98 B | 2.61 C |
| Pooled Studies AE-98-01/02 | 0.16 A | 2.12 B | 2.21 C |
| Time to Remed. (hrs.) (% who required remed.) | | | |
| Study AE-98-01 | 1.7 A (85%) | >12.0 B (48%) | >12.0 B (37%) |
| Study AE-98-02 | 1.6 A (95%) | >12.0 B (42%) | <12.0 B (34%) |
| Pooled Studies AE-98-01/02 | 1.6 A (90%) | >12.0 B (45%) | >12.0 C (35%) |
| Global Eval - Sleep-Aid[2] | | | |
| Study AE-98-01 | 0.53 A | 1.63 B | 1.76 B |
| Study AE-98-02 | 0.10 A | 1.57 B | 1.71 B |
| Pooled Studies AE-98-01/01 | 0.31 A | 1.60 B | 1.73 B |

Figure 28:
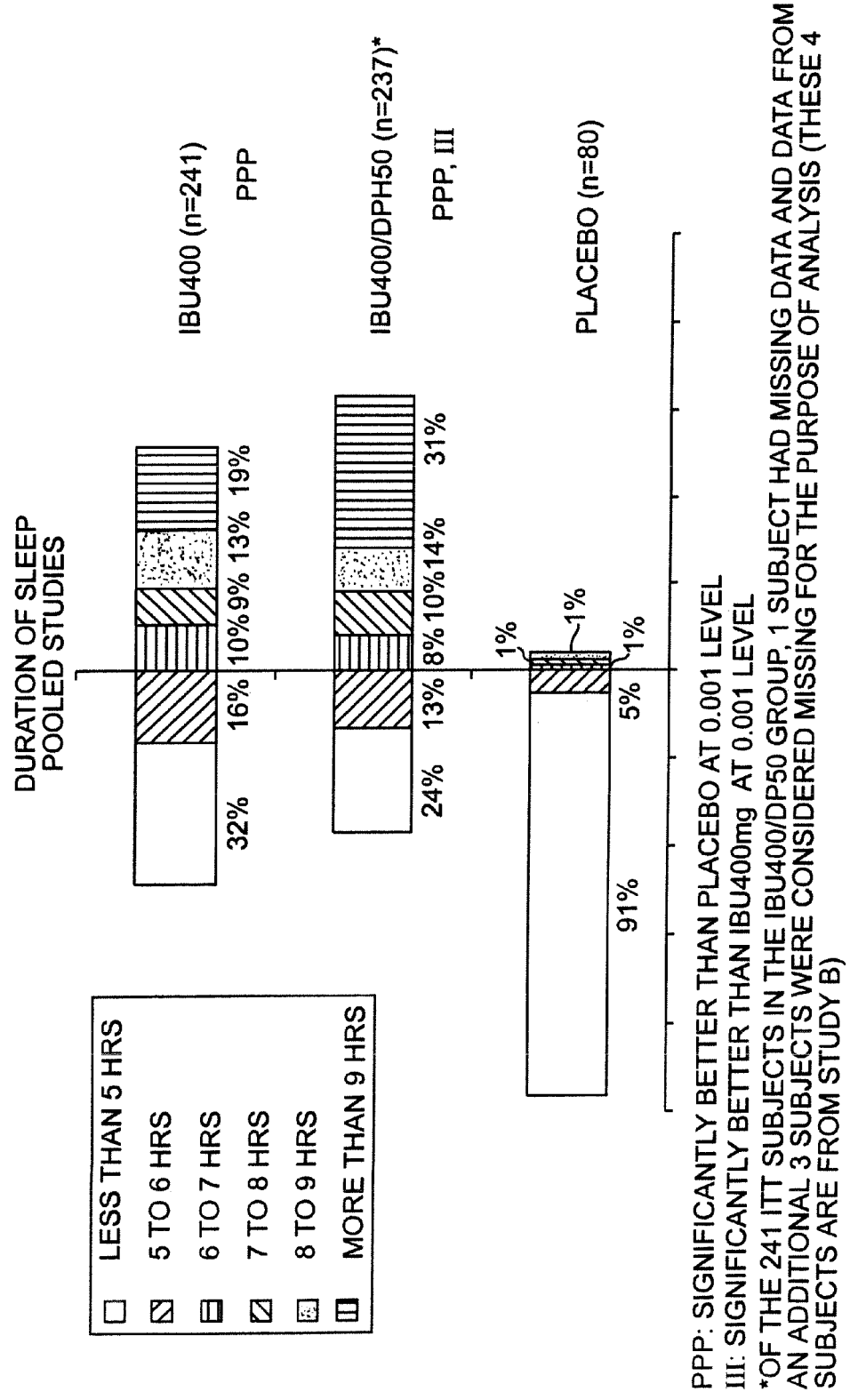
FIG. 28: This figure shows the duration of sleep data from pooling data.
Figure 29:
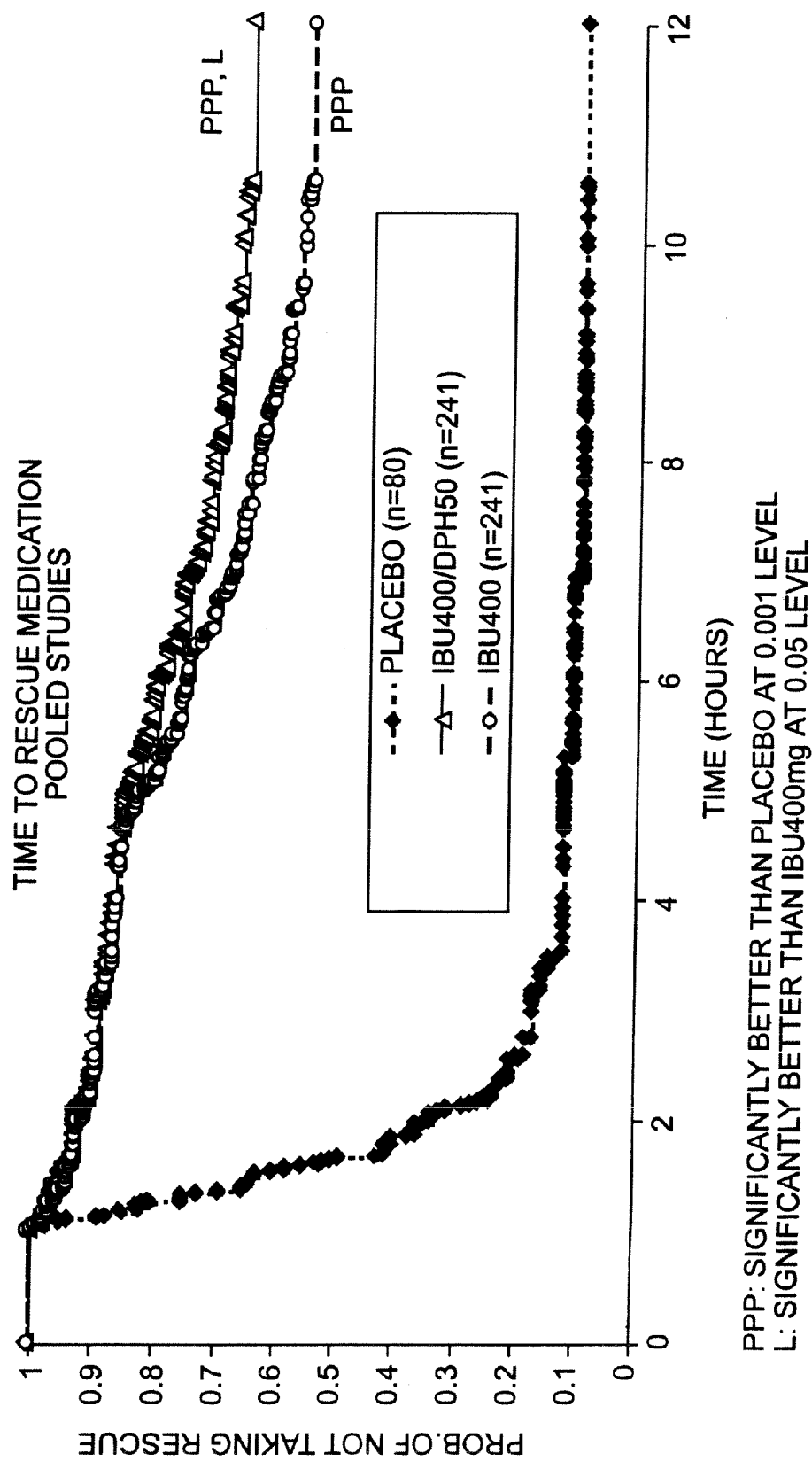
FIG. 29: This figure shows the time to rescue medication data from pooling data.

Note:
different letters indicate significant differences (at 0.05 level)
[1]assessed using a 6-point scale: 0 = <5 hrs; 1 = 5-6 hrs; 2 = 6-7 hrs; 3 = 7-8 hrs; 4 = 8-9 hrs; 5 = >9 hrs
[2]assessed using a 5-point categorical scale: 0-Poor to 4 = Excellent These data together show that those who received the combination slept about 30 minutes to 1 hour longer than those who received ibuprofen alone (FIG. 28). Fewer subjects who received the combination slept for less than 5 hours compared to those who received ibuprofen alone (24% vs. 32%, respectively). Fewer patients in the combination group required rescue medication compared to those who received ibuprofen only (FIG. 29). This difference was statistically significant when the data from the two studies were pooled (35% combination vs. 45% ibuprofen only).

Example 8

Treatment of Pain Associated Sleep Disturbances

Patients suffering from pain associated sleep disturbances were given 400 mg ibuprofen and 50 mg diphenhydramine in a single soft gelatin capsule formulation designed to prevent interactions between the compounds. Patients took the composition before bedtime and the symptoms of their pain associated sleep disturbances were improved. For example, they slept for a longer duration than expected, and they also fell asleep faster than expected. This shows that the composition of the invention is useful for treating pain associated sleep disturbances.

Example 9

Treatment of Pain Associated Sleep Disturbances

Patients suffering from pain associated sleep disturbances are given ibuprofen and diphenhydramine in a single formulation designed to prevent interactions between the compounds, according to the following table.

| Patient | Ibuprofen (mg) | Diphenhydramine HCl (mg) | Diphenhydramine Citrate (mg) | Formulation |
|---|---|---|---|---|
| 1 | 100 | 12.5 | 0 | PEG soft gelatin capsule |
| 2 | 100 | 12.5 | 0 | bilayer tablet |
| 3 | 100 | 0 | 19 | PEG soft gelatin capsule |
| 4 | 100 | 0 | 19 | bilayer tablet |
| 5 | 200 | 25 | 0 | PEG soft gelatin capsule |
| 6 | 200 | 25 | 0 | bilayer tablet |
| 7 | 200 | 0 | 38 | PEG soft gelatin capsule |
| 8 | 200 | 0 | 38 | bilayer tablet |
| 9 | 400 | 50 | 0 | PEG soft gelatin capsule |
| 10 | 400 | 50 | 0 | bilayer tablet |
| 11 | 400 | 0 | 76 | PEG soft gelatin capsule |
| 12 | 400 | 0 | 76 | bilayer tablet |
| 13 | 600 | 75 | 0 | PEG soft gelatin capsule |
| 14 | 600 | 75 | 0 | bilayer tablet |
| 15 | 600 | 0 | 75 | PEG soft gelatin capsule |
| 16 | 600 | 0 | 75 | bilayer tablet |
| 17 | 800 | 100 | 0 | PEG soft gelatin capsule |
| 18 | 800 | 100 | 0 | bilayer tablet |
| 19 | 800 | 0 | 100 | PEG soft gelatin capsule |
| 20 | 800 | 0 | 100 | bilayer tablet |

Patients take the composition before bedtime and the symptoms of their pain associated sleep disturbances are improved. For example, they sleep for a longer duration than expected, and they also fall asleep faster than expected. This shows that the composition of the invention is useful for treating pain associated sleep disturbances.

Example 10

Treatment of Pain Associated Sleep Disturbances

Patients suffering from pain associated sleep disturbances are given ibuprofen and diphenhydramine in a single formulation designed to prevent interactions between the compounds, according to the following table. Appropriate diphenhydramine citrate amounts are substituted easily for the diphenhydramine HCl, and either PEG soft gelatin capsules or bilayer tablets are effective.

| Patient | Patient Characteristics | Ibuprofen (mg) | Diphenhydramine HCl (mg) | Formulation |
|---|---|---|---|---|
| A | 90 lbs | 100 | 25 | PEG soft gelatin capsule |
| B | 150 lbs | 400 | 50 | PEG soft gelatin capsule |
| C | 250 lbs | 600 | 75 | PEG soft gelatin capsule |
| D | child | 100 | 12.5 | PEG soft gelatin capsule |
| E | adult | 400 | 50 | PEG soft gelatin capsule |
| F | elderly or medication sensitive | 100 | 25 | PEG soft gelatin capsule |

Patients take the composition before bedtime and the symptoms of their pain associated sleep disturbances are improved. For example, they sleep for a longer duration than expected, and they also fall asleep faster than expected. This shows that the composition of the invention is useful for treating pain associated sleep disturbances.

All references or patents cited in this specification are hereby incorporated by reference. The foregoing detailed description has been given for illustration purposes only. A wide range of changes and modifications can be made to the preferred embodiment described above. It should therefore be understood that it is the following claims, including all equivalents, are intended to define the scope of the invention.

We claim:

1. A solid dosage form comprising ibuprofen and diphenhydramine in amounts effective to treat a pain-associated sleep disturbance, wherein the solid dosage form has a bilayer configuration having a first layer and a second layer, wherein the first layer comprises all of the ibuprofen in an amount from 50 mg to 800 mg and the second layer comprises the diphenhydramine or a salt thereof in an amount from 12.5 mg to 50 mg.

2. The composition of claim 1, wherein the ibuprofen is present in an amount of 200 mg.

3. The composition of claim 1, wherein the diphenhydramine is present as diphenhydramine HCl or diphenhydramine citrate.

4. The composition of claim 3, wherein the diphenhydramine is present as diphenhydramine HCl or diphenhydramine citrate.

5. The composition of claim 4, wherein the diphenhydramine HCl is present in an amount of 25 mg.

6. The composition of claim 4, wherein the diphenhydramine citrate is present in an amount from 19 mg to 38 mg.

7. The composition of claim 6 wherein the diphenhydramine citrate is present in an amount of 38 mg.

8. The composition of claim 7, wherein the sleep disturbance affects sleep duration.

9. A composition to treat a pain-associated sleep disturbance comprising a liquid composition formulated inside a soft gelatin capsule, wherein said liquid composition consisting of about 200 to about 400 mg of ibuprofen and between about 10 to about 50 mg of diphenhydramine, and a solubilizing agent consisting of polyethylene glycol to prevent negative interactions between the ibuprofen and the diphenhydramine.

10. The composition of claim 9, wherein the ibuprofen is present in an amount of 200 mg.

11. The composition of claim 10, wherein the diphenhydramine is present as diphenhydramine HCl or diphenhydramine citrate.

12. The composition of claim 11, wherein the diphenhydramine is present as diphenhydramine HCl or diphenhydramine citrate.

13. The composition of claim 12, wherein the diphenhydramine HCl is present in an amount from 12.5 mg to 50 mg.

14. The composition of claim 13, wherein the diphenhydramine HCl is present in an amount of 25 mg.

15. The composition of, claim 11 wherein the diphenhydramine citrate is present in amount from 19 mg to 38 mg.

16. The composition of claim 15, wherein the diphenhydramine citrate is present in an amount of 38 mg.

17. The composition of claim 9, wherein the sleep disturbance affects sleep duration.

18. A solid dosage form comprising ibuprofen and diphenhydramine in amounts effective to treat a pain-associated sleep disturbance, wherein the solid dosage form has a configuration having a first layer and a second layer, wherein the first layer comprises all of the ibuprofen and the second layer comprises the diphenhydramine or a salt thereof, thereby minimizing the negative interaction between the diphenhydramine and the ibuprofen, wherein the solid dosage form further comprises at least one of calcium stearate, croscarmellose sodium, glyceryl behenate, lactose, microcrystalline cellulose, silicon dioxide colloidal, sodium lauryl sulfate, sodium starch glycolate, corn starch, preglatinized starch, starch or stearic acid.

* * * * *